(12) United States Patent
Brown et al.

(10) Patent No.: US 8,349,297 B2
(45) Date of Patent: Jan. 8, 2013

(54) TOPICAL FORMULATIONS

(75) Inventors: Marc Barry Brown, Watford (GB); Stuart Allen Jones, Blackheath (GB)

(73) Assignee: Medpharm Limited, Guilford (GB)

(*) Notice: Subject to any disclaimer, the term of this patent is extended or adjusted under 35 U.S.C. 154(b) by 812 days.

(21) Appl. No.: 12/067,004

(22) PCT Filed: Sep. 14, 2006

(86) PCT No.: PCT/GB2006/003408
§ 371 (c)(1),
(2), (4) Date: Jul. 16, 2008

(87) PCT Pub. No.: WO2007/031753
PCT Pub. Date: Mar. 22, 2007

(65) Prior Publication Data
US 2009/0191271 A1 Jul. 30, 2009

(30) Foreign Application Priority Data
Sep. 14, 2005 (GB) .................................. 0518769.5

(51) Int. Cl.
*A61K 9/12* (2006.01)
(52) U.S. Cl. ......................................................... 424/45
(58) Field of Classification Search ...................... 424/45
See application file for complete search history.

(56) References Cited

U.S. PATENT DOCUMENTS

| | | | |
|---|---|---|---|
| 4,752,466 A | 6/1988 | Saferstein et al. |
| 4,863,721 A | 9/1989 | Beck et al. |
| 5,776,432 A | 7/1998 | Schultz et al. |
| 6,123,924 A | 9/2000 | Mistry et al. |
| 6,325,990 B1 | 12/2001 | Laurent |
| 6,432,415 B1 | 8/2002 | Osborne et al. |
| 2003/0152611 A1 | 8/2003 | Illel et al. |
| 2003/0224053 A1 | 12/2003 | Fotinos et al. |
| 2004/0184994 A1 | 9/2004 | Destefano et al. |
| 2004/0213744 A1 | 10/2004 | Lulla et al. |
| 2011/0002856 A1* | 1/2011 | Holland et al. ................. 424/45 |

FOREIGN PATENT DOCUMENTS

| | | |
|---|---|---|
| AU | 198664695 | 5/1988 |
| GB | 2188844 | 10/1987 |
| JP | 01230514 | 9/1989 |
| JP | 08291050 | 11/1996 |
| WO | WO 88/09185 | 12/1988 |
| WO | WO 95/15151 | 6/1995 |
| WO | WO 00/38658 | 7/2000 |
| WO | WO 00/45795 | 8/2000 |
| WO | WO 01/43722 | 6/2001 |

OTHER PUBLICATIONS

"Miscible" in Merriam-Webster's Collegiate Dictionary, 10th edition, Merriam-Webster, Inc.: Springfield, Mass., 1993, pp. 743.*
Brambilla et al. (1999) "Modulation of Aerosol Clouds Produced by Pressurized Inhalation Aerosols," *Int. J. Pharmaceutics* 186:53-61.
Hadgraft, J. (2004) "Skin Deep," *Eur. J. Pharm. Biopharm.* 58:291-299.
International Search Report, Corresponding to International Application No. PCT/GB2006/003408, Mailed Feb. 27, 2007.
Moser et al. (2001) "Supersaturation: Enhancement of Skin Penetration and Permeation of a Lipophilic Drug," *Pharm. Res.* 18(7):1006-1011.
Moser et al. (May 2001) "Permeation Enhancement of a Highly Lipophilic Drug Using Supersaturated Systems," *J. Pharm. Sci.* 90(5):607-616.
Moser et al. (2001) Stabilization of Supersaturated Solutions of a Lipophilic Drug for Dermal Delivery,: *Int. J. Pharm.* 224:169-176.
Ranade, V.V. (1995) "Transdermal Drug Delivery," In; *Drug Delivery Systems*, CRC Press, New York, pp. 177-208.
Thomas et al. (Aug. 2004) "The Transdermal Revolution," *Drug Disc. Today* 9(16):697-703.
Ting et al. (2004) "Review of Traditional and Novel Modalities that Enhance the Permeability of Local Therapeutics Across the *Stratum corneum*," *Int. J. Dermatol.* 43:538-547.
Vervaet et al. (1999) "Drug-Surfactant-Propellant Interactions in HFA-Formulations," *Int. J. Pharm.* 186:13-30.
Yong-Hong Liao (Jul. 2002) "Studies on the Stabilization and Formation of Proteins for Airway Delivery," PhD. Thesis, University of London, Department of Pharmacy, King's College London.

* cited by examiner

Primary Examiner — James H. Alstrum-Acevedo
(74) Attorney, Agent, or Firm — Greenlee Sullivan P.C.

(57) ABSTRACT

Saturated, monophasic solutions of drug in a solvent and propellant mixture, together with a film-forming agent, exhibit transdermal diffusion fluxes greater than those predicted by Fick's law when applied topically.

33 Claims, 14 Drawing Sheets

TOPICAL FORMULATIONS

CROSS-REFERENCE TO RELATED APPLICATIONS

Figure 1:
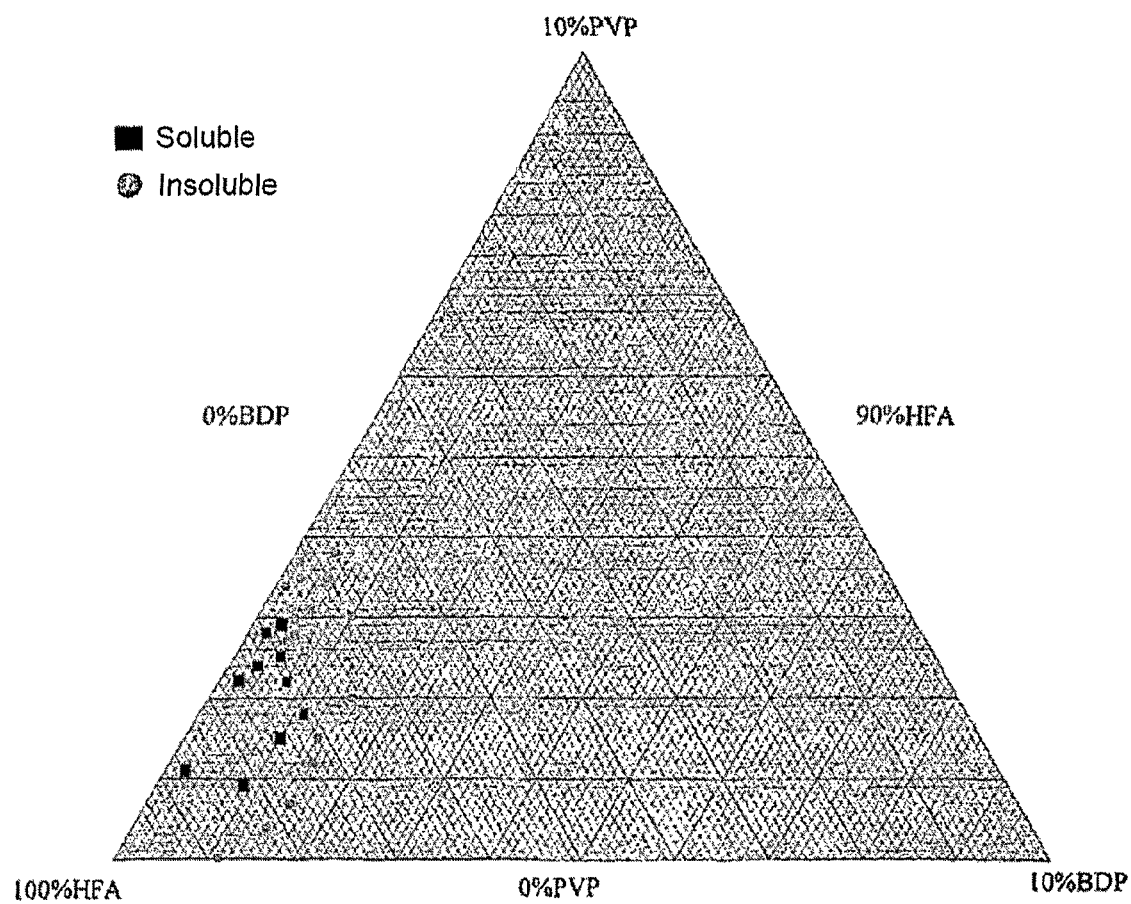

This application is a 35 U.S.C. 371 National Phase Application of PCT/GB2006/003408, filed Sep. 14, 2006, which application claims benefit of GB 0518769.5, filed Sep. 14, 2005.

The present invention relates to formulations for topical drug delivery, and methods for their use and manufacture.

The administration of therapeutic compounds either locally to the skin, or into the systemic circulation after passage through the skin, offers numerous potential advantages over oral or parenteral drug delivery. These include the avoidance of hepatic first-pass metabolism, improved patient compliance and ease of access to the absorbing membrane, i.e. the skin. In addition, in the case of local delivery (i.e. delivery to the superficial layers of the skin) by directly administering the drug to the pathological site, any adverse effects associated with systemic toxicity can be minimised. However, the effective delivery of drugs into and through the skin is not trivial.

Molecules can pass into and/or through the skin via passive diffusion. Passive diffusion can be described thermodynamically by Fick's first law:

$$J = \frac{KD(c_{app} - c_{rec})}{h} \quad [1]$$

where (J) describes the steady state flux per unit area, (K) is the partition of the drug between the skin and the formulation and (D) is the diffusion coefficient through the diffusional path length (h). Since usually the concentration of the permeate in the applied dose ($c_{app}$) is so much higher than the concentration in the receptor phase ($c_{rec}$) this equation can be simplified to:

$$J = k_p c_{app} \quad [2]$$

where $k_p$ is the permeability coefficient and equal to KD/h (Hadgraft, 2004). According to Fick's law the most important factors that influence flux across the skin are the concentration gradient of the drug within the skin, the partition coefficient of the permeate and the diffusion coefficient (Thomas and Finnin, 2004; Hadgraft, 2004). In addition, the flux (J) of a molecule across a membrane should increase linearly with concentration until $c_{app}$ reaches the solubility limit i.e. at the point of saturation (i.e. a thermodynamic activity (TA) of 1. Assuming there is no interaction between the drug and the delivery vehicle, then this means that, regardless of 1) the nature of the vehicle in the drug saturated formulation, and 2) the quantity of a drug saturated formulation applied to the membrane at a TA=1, the flux/release of the drug will remain the same. Thus, when a saturated drug formulation is applied to the skin, the drug will be at its highest thermodynamic activity, in accordance with Fick's law. In some instances TA can exceed 1 when supersaturated systems are formed. However, such formulations are inherently unstable and as such are not suitable for use in vivo.

Human skin comprises three tissue layers: 1) the stratified, avascular, cellular epidermis; 2) the underlying dermis of connective tissue; and 3) the subcutaneous fat beneath the dermis. The physiological function of the Stratum corneum, the outermost and non-viable layer of the skin, is to act as a protective barrier for the body. The Stratum corneum's intercellular lipids comprise ceramides, cholesterols, cholesterol esters, and free fatty acids, whose organisation and unique chemical composition create a high degree of water impermeability. It is these lipid lamellae that contribute greatly to the epidermal permeability barrier, both to water and to other permeates (Ting et al., 2004).

In order for therapeutic quantities of drug to penetrate the skin, the barrier properties of the Stratum corneum must be overcome. The Stratum corneum exhibits selective permeability and allows only relatively lipophilic compounds with a molecular weight below 400 Daltons to pass. However, where a drug is very lipophilic, it may cross the Stratum corneum, but diffusion is rapidly slowed as it enters the more aqueous lower regions of the epidermis in which it is poorly soluble. Thus, as the diffusion of a very hydrophobic permeate proceeds into deeper layers of the skin, diffusion slows, and the concentration gradient (from Stratum corneum down to the viable tissue) falls. The rate-determining step for species diffusing in this manner then becomes barrier clearance not barrier penetration.

In addition to their inability to penetrate into the deep layers of the epidermis, poorly water soluble molecules are also notoriously difficult to formulate as they often exhibit low solubility in numerous topical vehicles. A sufficient concentration of a topically applied therapeutic agent must be loaded into the vehicle to ensure an adequate concentration gradient between the formulation and the skin, in order to attain adequate release of the drug into the skin. Topical formulations, such as ointments, which can solubilise high concentrations of hydrophobic actives, are "heavy" and "greasy", thus making them cosmetically unacceptable. However, the low solubility of hydrophobic compounds in more cosmetically acceptable topical vehicles such as creams and gels often precludes their use.

Methods of overcoming the barrier properties of the Stratum corneum may be divided into chemical, such as the use of occlusion, penetration enhancers and supersaturated systems, and physical, such as iontophoresis, skin electroporation, ultrasound and powder injection methods. For small organic molecules, chemical enhancement methods have several advantages, in terms of their low cost, lack of irritancy, and simplicity, compared to physical methods.

Irrespective of their mode of action, penetration enhancers usually alter the barrier properties of the skin. Whether the structural alteration is reversible or not, the concentrations of penetration enhancers required to elicit an efficacious response often causes skin irritation, unwanted side effects, and/or drug instability. Thus, whilst many penetration enhancers are undoubtedly effective, they can often be difficult to formulate and impractical to use.

The Stratum corneum is only approximately 10 μm thick when dry, but it swells significantly in the presence of water. Hydration of the Stratum corneum softens the skin by loosening the lipid packing which makes it more easily traversed by a lipid-like penetrant. Occlusion is a popular and simple way to hydrate the skin and is commonly achieved by either applying a patch or a very hydrophobic vehicle to prevent transepidermal water loss. However, as previously discussed, hydrophobic vehicles are cosmetically unacceptable and because of solubility issues most patches only deliver about 10% of the total dose, with the subsequent 90% of the drug remaining in the patch being discarded.

According to Fick's first law, the flux of a drug (assuming no interaction with the vehicle) is directly proportional to its thermodynamic activity in the formulation, which is related to the degree of saturation. If a topical vehicle is supersaturated with a drug i.e. the maximum concentration of drug that can be dissolved in a vehicle is increased using complimentary excipients and/or variations in the pH, temperature, or the formulation vehicle, flux is increased as a direct result of an increase in the thermodynamic activity (Moser et al., 2001a). However, whilst supersaturated systems are thermodynamically more active, they are typically thermodynamically unstable and crystallisation of the drug often occurs with time, which is not acceptable within a pharmaceutical product.

One method to overcome the problem of the thermodynamic instability within supersaturated systems is to create the supersaturation from subsaturated solutions immediately before or during topical application. This can be accomplished by water uptake from the skin, evaporation of a volatile solvent, or using a mixed cosolvent system, where the vehicle changes are created prior to administration of the formula (Moser et al., 2001b).

Creating supersaturated systems using volatile solvents is a very effective method of increasing thermodynamic activity. However, the volatile solvent must ideally be non-toxic, non-combustible, have excellent solubility properties for a wide range of drugs, and be inert. In addition, the final supersaturated system should contain an anti-nucleating agent to slow down the process of crystallisation to retain optimal thermodynamic activity. It has been shown that the addition of polymers/plasticisers can be used to slow the process of recrystallisation. The following polymers have previously been used to effectively prevent recrystallisation of a number of drugs in supersaturated solutions: Eudragit R/S 100 L, HPMC phthalate, ethyl cellulose, methyl cellulose, cyclodextrin, hydroxypropyl cellulose, poly(vinyl pyrrolidone) (PVP), poly (vinyl alcohol) (PVA), and carboxymethyl cellulose. Supersaturated formulas are, generally, best stabilised by polymers having similar solubility parameters to the drugs themselves, since those having higher values can have a destabilising effect. However, matching solubility parameters is not yet a reliable method for predicting an optimal supersaturated formulation (Moser et al., 2001c).

At present, the majority of volatile topical sprays employ a short chain hydrocarbon such as butane, propane, n-butane, or a mixture thereof, as the delivery vehicle. These solvents have been approved by the US Food and Drug Administration (FDA) for topical use and are generally accepted as safe (GRAS listed by the FDA). However, whilst hydrocarbon aerosol propellants are relatively inexpensive, non-toxic, and environmentally friendly (since they are not damaging to the ozone layer and are not greenhouse gases) their use is limited by their flammability. Butane, especially, is explosive and must only be handled in an explosion-proof room which is equipped with adequate safety warning devices and explosion-proof equipment.

Hydrofluoroalkane (HFA) solvents have been approved for human use in pressurised metered dose inhalers (pMDIs) since the mid 1990's (Vervaet and Byron, 1999). These solvents are highly volatile, like hydrocarbons, but are non-combustible. HFAs were developed specifically to replace chlorofluorocarbon (CFC) solvents, which were found to have damaging effects on the ozone layer. However, the boiling point, Kauri-Butanol value, dielectric constant, dipole moment, polarisability and solubility parameters of HFA and CFC propellants differ significantly (c.f. table 1).

TABLE 1

Physical properties of CFC and HFA propellants.

|  | BP | KB | δ | μ | ε | α |
|---|---|---|---|---|---|---|
| CFC 11 | 23.8 | 60 | 7.6 | 0.46 | 2.3 | 9.5 |
| CFC 12 | −29.8 | 18 | 6.1 | 0.51 | 2.1 | 7.9 |
| CFC 114 | 3.6 | 12 | 6.4 | 0.50 | 2.3 | 8.5 |
| HFA 134a | −25.8 | 8 | 6.6 | 2.06 | 9.5 | 5.4 |
| HFA 227ea | −17.3 | 10 | 6.6 | 0.93 | 4.1 | 5.8 |

BP: boiling point ° C.;
KB: Kauri-Butanol value;
δ: solubility parameter cal/ml;
μ: dipole movement;
ε: dielectric constant;
α: polarisability (adapted from Vervaet and Byron, 1999)

These differences are caused in part by the enhanced electronegativity of HFAs (fluorine is more electronegative than chlorine). The strong electron drawing potential of the fluorine atoms minimises the intermolecular attraction in these propellants which leads to a lower boiling point compared to structurally equivalent CFC propellants. In addition, the asymmetrically positioned hydrogen atoms within the structure of HFAs creates a distinct dipole on the hydrogen-carbon bonds in both propellants. The increased polarity of the HFA propellants is reflected in their larger dipole moment and dielectric constant compared to CFCs.

Thus, whilst HFA propellants are ideal in terms of safety and volatility to use for topical sprays, their unique blend of hydrophobic and electronegative properties means that, unlike the hydrocarbons or the CFCs, they are incapable of solubilising a wide range of both hydrophilic and hydrophobic therapeutic agents. Their lack of solubility for the majority of therapeutic compounds precludes their use alone as a volatile vehicle for topical sprays.

In order to improve the solubility profile of HFA propellants, co-solvents can be used. However, again the co-solvent system must display excellent topical tolerability, should be volatile, acceptable as a pharmaceutical excipient and be able to solubilise a wide range of therapeutic agents. In previous work, in the investigation of solution MDIs, ethanol has been used as a co-solvent (Brambilla, 1999). Ethanol solubilises a wide range of therapeutic agents and is acceptable for use in therapeutic formulations.

In U.S. Pat. No. 6,123,924, PVP is disclosed as a suspending agent to aid the suspension of therapeutic agents for inhalable drug delivery.

In WO 95/15151, there is disclosed pharmaceutical formulations for aerosol delivery and comprising the therapeutic agent in combination with a protective colloid, which may include PVA, and an HFA.

In U.S. Pat. No. 5,776,432 there is disclosed the use of HFA and ethanol to solubilise a steroid.

US 2003/0224053 discloses compositions which can form a film in contact with skin and which comprise a polymer, an active ingredient and a solvent to provide a patch that can be peeled off and that will deliver a useful amount of drug or cosmetic. There is no requirement that the composition be monophasic or that the active ingredient is saturated.

US 2003/0152611 discloses pharmaceutical compositions for transdermal administration comprising a cellulosic polymer matrix, an NSAID, an absorption promoter, water and a solvent forming matrix. Monophasic saturated solutions are not required.

U.S. Pat. No. 6,432,415 discloses bioadhesive gels and aerosols comprising a water-insoluble, pharmaceutically acceptable alkyl cellulose, a solvent system comprising a volatile solvent and water, a solubilising agent and a pharmaceutical. It is possible to incorporate a propellant. There is no suggestion that the preparations be either monophasic or saturated.

U.S. Pat. No. 6,325,990 provides lipophilic vitamins etc. in the absence of water and in the presence of adhesive polysiloxane, an absorption promoter and a volatile solvent, sprayable from an aerosol can. There is no suggestion that the compositions should be either monophasic or saturated.

WO 0/045795 provides medicinal spray compositions comprising a medicament in a volatile vehicle and one or more film-forming polymers. There is no suggestion that the compositions should be either monophasic or saturated.

WO 0/38658 discloses slimming compositions for dermal administration comprising a matrix which forms a soft film after drying. There is no disclosure that the compositions should be either monophasic or saturated.

JP 08291050 discloses an aerosol composition having foaming activity. The composition comprises an acrylic polymer, a plasticiser, a lower alcohol, water, a surfactant, a propellant and polyvalent alcohol. There is no suggestion that the compositions should be either monophasic or saturated.

JP 01230514 provides an aerosol type patch comprising a film forming polymer, a solvent, a propellant and drug. There is no suggestion that the compositions should be either monophasic or saturated.

WO 88/09185 discloses a dressing comprising a film-forming polymer which contains the active ingredient, a liquid polymer matrix which forms the flexible film on hardening, and a solvent controlling release of the active ingredient, together with a solvent for the matrix, and a propellant. The compositions are not monophasic and concentration is not a significant factor.

AU 198664695 provides a pesticide composition comprising a film-forming polymer, a solvent and an active material. A clear solution is described as being desirable for use as an aerosol, but saturation is not suggested or required.

GB 2188844 discloses an anti-psoriatic composition comprising a liquid formulation of film forming polymers together with anti-psoriatic compounds. There is no disclosure that the compositions should be either monophasic or saturated.

Surprisingly, we have now discovered that saturated, monophasic solutions of drug in a solvent and propellant mixture, together with a film-forming agent, exhibit passive diffusion fluxes greater than those predicted by Fick's law.

Thus, in a first aspect, the present invention provides a pharmaceutical formulation capable of forming a film on topical administration, said formulation comprising a preparation of a pharmaceutical, a solvent therefor, a film-forming agent, and a propellant, wherein the formulation is monophasic and the pharmaceutical is present in a saturating amount therein, under conditions of use.

The term 'monophasic' is used to indicate that the formulation does not contain undissolved drug, and also that there is only the one liquid phase, and not a colloid or micro-colloid, for example. There is only one phase, and that phase is liquid.

The drug should be present in a saturating amount in the formulation. In this respect, it will be appreciated that a formulation held at a higher temperature will require greater amounts of drug in order to be saturated, for most solvents. In this regard, the monophasic requirement remains important, but saturation may be determined by whether the formulation, when applied to a test membrane such as disclosed in the accompanying Examples, transcends Fick's law or only provides a flux at or below that predicted by Fick's law.

Thus, by saturated we also include substantially saturated, wherein at least 80% of that amount of the drug needed to achieve saturation is present. This amount is preferably at least 90%, and more preferably 95%. At the temperature of use, it is preferred that the formulation be as close to saturated as possible, while remaining monophasic. Supersaturated solutions are also included, but these are generally less preferred, as they are not generally stable, and have short shelf-lives before ceasing to be monophasic.

It is preferred that the amount of drug present be as close to full saturation as possible, but many monophasic solutions are not stable at such high concentrations. In such cases, the addition of antinucleating agents, such as are described below, may be advantageous, as may a slight drop in saturation, down as far as 80%, which is considered to be a saturating amount for the purposes of the present invention.

The advantage of the present invention lies in the combined high saturation levels and the use of propellant. The propellant is typically a highly volatile liquid with a low boiling point, such as a CFC or HFA, and particularly HFA (hydrofluoroalkane), such that it can force the formulation from a dispenser. Evaporation is almost instantaneous and the boiling during transfer from the dispenser to the site of administration has the effect of causing the evaporation of a substantial amount of the solvent, which are as defined below, but is typically ethanol or isopropyl alcohol. Thus, the solvent is preferably a volatile solvent, and is preferably more volatile than water and will often be organic, and the almost explosive decompression of the propellant causes the disruption and loss of solvent by evaporation. This loss can be up to 50% and even higher.

The effect of the loss of solvent is to drive the remaining solution towards supersaturation. It is for this reason that saturation levels of at least 80% are necessary, as levels much below this tend to result in saturated solutions rather than supersaturated solutions, and little advantage is to be seen. At 80% and above, levels of supersaturation of up to 2.5 times saturation may be achieved, with the concomitant ability to drive permeation across the Stratum corneum. Lower levels of saturation require greater loss of solvent before supersaturation is achieved.

The pharmaceutical may be any substance for which it is desired to achieve penetration into and/or through the skin, and such substances will generally also be referred to herein as 'drugs'. Suitable drugs for use in accordance with the present invention include, but are not limited to, those in the following Table, either individually or in combination:

| Type Of Drug | |
|---|---|
| Local antipruritics | Crotamiton |
| | Doxepin hydrochloride |
| | Mesulphen |
| | Polidocanol |
| Local anaesthetics | Amethocaine (Hydrochloride in solutions or creams, base in gels or ointments) |
| | Amylocaine (Hydrochloride) |
| | Benzocaine |
| | Bucricaine (hydrochloride) |
| | Butacaine Sulphate |
| | Butyl Aminobenzoate Picrate |
| | Cincocaine (base, hydrochloride or benzoate) |
| | Dimethisoquin Hydrochloride |
| | Dyclocaine Hydrochloride |
| | Ethyl Chloride |
| | Lidocaine |
| | Lignocaine |
| | Myrtecaine |
| | Oxethazaine (Oxetacaine) |
| | Prilocaine |
| | Propanocaine Hydrochloride |
| | Tetracaine |
| Antihistamines | Antazoline |
| | Chlorcyclizine Hydrochloride |
| | Dimethindene Maleate |
| | Diphenhydramine |
| | Histapyrrodine |
| | Isothipendyl Hydrochloride |
| | Mepyramine |
| | Mepyramine Maleate |
| | Tolpropamine Hydrochloride |
| | Tripelennamine Hydrochloride |
| | Triprolidine Hydrochloride |
| Corticosteroids | Alclometasone dipropionate |
| | Beclomethasone dipropionate |
| | Betamethasone valerate |
| | Clobetasol propionate |
| | Clobetasone butyrate |
| | Desoximetasone |
| | Diflucortolone valerate |
| | Fludroxycortide/Flurandrenolone |
| | Fluocinolone acetonide |
| | Hydrocortisone |
| | Hydrocortisone acetate |
| | Hydrocortisone butyrate |
| Topical preparations for psoriasis | Calcipotriol |
| | Coal tar |
| | Dithranol |
| | 5-Fluouracil |
| | Ciclosporin |
| | Fumeric acid |
| | Lonapalene |
| | Methotrexate |
| | Methoxsalen |
| | Salicylic acid |
| | Tacalcito |
| | Tacrolimus |
| | Pimecrolimus |
| | Tazarotene |
| Topical preparations for acne | Azelaic acid |
| | Benzoyl peroxide |
| | Dithiosalicylic acid |
| | Motretinide |
| | Resorcinol |
| Topical antibacterials for acne | Clindamycin |
| | Erythromycin |
| 'Dermatological drugs' | Becaplermin (Diabetic skin ulcers) |
| | Bentoquatum (prevents allergic contact dermatitis caused by poison ivy) |
| | Gamolenic acid |
| | Glycolic acid (Photodamaged skin) |
| | Hydroquinone/Mequinol (Depigmenting agents) |
| | Ichthammol |
| | Keluamid (seborrhoeic dermatitis) |
| | Lithium succinate |
| | Monobenzone (vitiligo) |
| | Polyphloroglucinol Phosphate (Treatment of wounds and pruritic skin disorders) |
| | Sodium pidolate (humectant, applied as cream/lotion for dry skin disorders) |
| | Sulphur (mild antifungal/antiseptic) |
| | Sulphurated Lime (For acne, scabies, seborrhoeic dermatitis) |
| | Sulphurated Potash (Acne) |
| | Minoxidil (hair growth) |
| Topical retinoids and related preparations for acne | Adapalene |
| | Isotretinoin |
| | Polyprenoic acid |
| | Tretinoin |
| Other topical preparations for acne | Nicotinamide |
| Topical antibacterials | Amphomycin |
| | Bacitracin/Bacitracin Zinc |
| | Bekanamycin Sulphate |
| | Chloramphenicol |
| | Chlorquinaldol |
| | Chlortetracycline |
| | Framycetin sulphate |
| | Fusidic Acid |
| | Halquinol |
| | Mupirocin |
| | Mupirocin |
| | Neomycin sulphate |
| | Polymyxins (Polymyxin B Sulphate) |
| | Silver sulphadiazine (sulfadiazine) |
| | Sulphanilamide |
| | Sulphasomidine |
| | Sulphathiazole (sulfathiazole) Sodium |
| Topical antifungals | Benzoyl peroxide |
| | Amorolfine |
| | Benzoic acid |
| | Bifonazole |
| | Bromochlorosalicylanilide |
| | Buclosamide |
| | Butenafine Hydrochloride |
| | Chlormidazole Hydrochloride |
| | Chlorphenesin |
| | Ciclopirox Olamine |
| | Clotrimazole |
| | Croconazole Hydrochloride |
| | Eberconazole |
| | Econazole nitrate |
| | Fenticlor |
| | Fenticonazole Nitrate |
| | Flutrimazole |
| | Haloprogin |
| | Ketoconazole |
| | Mepartricin |
| | Miconazole nitrate |
| | Naftifine Hydrochloride |
| | Natamycin |
| | Neticonazole Hydrochloride |
| | Nystatin |
| | Omoconazole Nitrate |
| | Oxiconazole Nitrate |
| | Pyrrolnitrin |
| | Sertaconazole Nitrate |
| | Sodium Propionate |
| | Sulbentine |
| | Sulconazole nitrate |
| | Sulconazole Nitrate |
| | Terbinafine |
| | Tioconazole |
| | Tolciclate |
| | Tolnaftate |
| | Triacetin |
| | Undecenoates/Undecanoic Acid |
| Antiviral preparations | 1-Docosanol |
| | Aciclovir |
| | Brivudine |
| | Edoxudine |
| | Ibacitabine |
| | Idoxuridine |
| | Idoxuridine in dimethyl sulfoxide |

-continued

| Type Of Drug | |
|---|---|
| | Imiquimod |
| | Penciclovir |
| | Vidarabine |
| Parasiticidal preparations | Benzyl benzoate |
| | Carbaryl |
| | Malathion |
| | Permethrin |
| | Phenothrin |
| Preparations for minor cuts and abrasions | Cetrimide |
| | Collodion |
| | Magnesium sulphate |
| | Proflavine |
| Topical circulatory preparations | Heparinoid |
| Transdermal drugs | Ibuprofen |
| | Diclofenac |
| | Glyceryl trinitrate |
| | Oxybutynin |
| | Nicotine |
| | Ethinylestradiol + norelgestronin |
| | Griseofulvin |
| | Hyoscine |
| | Alfentanil |
| | Fentanyl |
| | Remifentanil |
| | Testosterone |
| | Oestrogen |
| | Methylphenidate hydrochloride |
| | Prednisolone |
| | Methyl prednisolone |
| Antiperspirants | Aluminium chloride |
| | Glycopyrronium bromide |

Other suitable drugs include the non-steroidal anti-inflammatories (NSAIDs), actinic keratosis treatments, and capsaicin, as well as such other substances as menthol. It will be appreciated that the pharmaceutical may be suitable either for local or systemic application.

Topical administration will generally include any exposed position on the body where it may be advantageous to administer a formulation of the invention. The highly volatile nature of the propellant will normally restrict such administration to intact skin, including contusions and bruises, but the invention also envisages, in a less preferred aspect, the administration of formulations to any topical membrane, and to lesions or wounds.

The formulations of the invention are capable of forming a film on topical administration, typically to the skin. In particular, the majority of the propellant component of the formulation will normally evaporate almost immediately, thereby concentrating the remainder of the formulation. The film-forming component may be such as to form a film substantially in the absence of the propellant or, more preferably, after the evaporation of a portion of the solvent.

The film-forming component may suitably be a polymer approved for topical administration, such as polyvinyl pyrrolidone (PVP) or polyvinyl alcohol (PVA), for example.

Without being restricted by theory, it is believed that the formation of a film serves to occlude the skin, and to encourage the retention of water in the skin. This has the advantage that water in the skin may continue to interact with the drug after evaporation of the solvents, thereby to continue permeation of the drug. Thus, a film-forming agent that is capable of forming a hydrogel is preferred. In this respect, PVP and PVA are preferred. Other, suitable, film forming agents include; acrylic polymers or copolymers, methacrylate polymers and copolymers, poly (vinyl acetate), and cellulose based polymers and co-polymers.

The film-forming agent typically also serves the role of anti-nucleating agent as the formulation grows more concentrated once it has been dispensed. However, it may be desired to further inhibit nucleation of the drug, in which case a further component may be added to the formulation for this purpose, always provided that the formulation is monophasic and saturated with drug under conditions of use. Suitable anti-nucleating agents are well known in the art, and may include PVA when PVP is used as the film-forming agent. Other suitable anti nucleating agents include methyl cellulose, ethyl cellulose, hydroxyalkylcelluloses, such as hydroxypropylmethylcellulose and hydroxypropylcellulose, glycol esters, polyacrylic acid, and derivatives thereof.

Plasticisers may also usefully be added to the formulation, where the resulting film would be less flexible than desirable. Plasticisers are well known in the art, and include water, glycerol, oleic acid, citric acid, phosphate esters, fatty acid esters, glycol derivatives, hydrocarbons and hydrocarbon derivatives, adipic acid/butanediol polyesters, epoxidised soya oils, diethyl phthalate, dibutyl phthalate, citric acid esters such as triethyl citrate and the like, castor oil, triacetin and chlorinated paraffins.

Components other than the drug, solvent, propellant and film-forming agent are also referred to herein as excipients.

It will be appreciated that the formulation will be saturated with drug and be monophasic under conditions of use. In this respect, these requirements relate to the formulation immediately prior to dispensing, such as when in an aerosol canister.

We have established that it is extremely important that the drug be present in saturating concentrations in the formulation, at the time of use, and that the formulation be monophasic. It is especially surprising that formulations containing differing amounts of all of the same components, but wherein the drug is in a higher, but not saturating concentration, perform considerably worse than those having a lower, but saturated concentration.

The propellant may be an HFA, as illustrated above. The HFA will normally play more of a part than a merely neutral and unreactive diluent, and will generally act as a cosolvent, albeit a poor one, for the most part. For purposes of convenience, it will also be appreciated that the propellant will normally be added last. Thus, as is demonstrated in the accompanying Examples, where ethanol is used as the primary solvent, for example, and the final concentration of ethanol is 10% in relation to the final composition, then PVP as a film-forming agent can only be added to a final concentration of no more than about 2% if a drug such as beclomethasone dipropionate (BDP) is used. In such a formulation, the HFA will form around 87-88% of the formulation.

However, where the amount of HFA that is added to precisely the same pre-mix is such that the final amount of ethanol is 20% rather than 10%, then the resulting formulation will not be saturated for BDP.

It will be appreciated that where HFA is referred to herein, then this includes reference to any suitable propellant unless otherwise indicated. It will also be appreciated that HFA may serve as an anti-solvent in some instances, so that when added to a saturated ethanolic solution of drug, for example, it may force precipitation, and such properties of HFA are usefully taken into account when preparing the final saturated solution.

Figure 19:
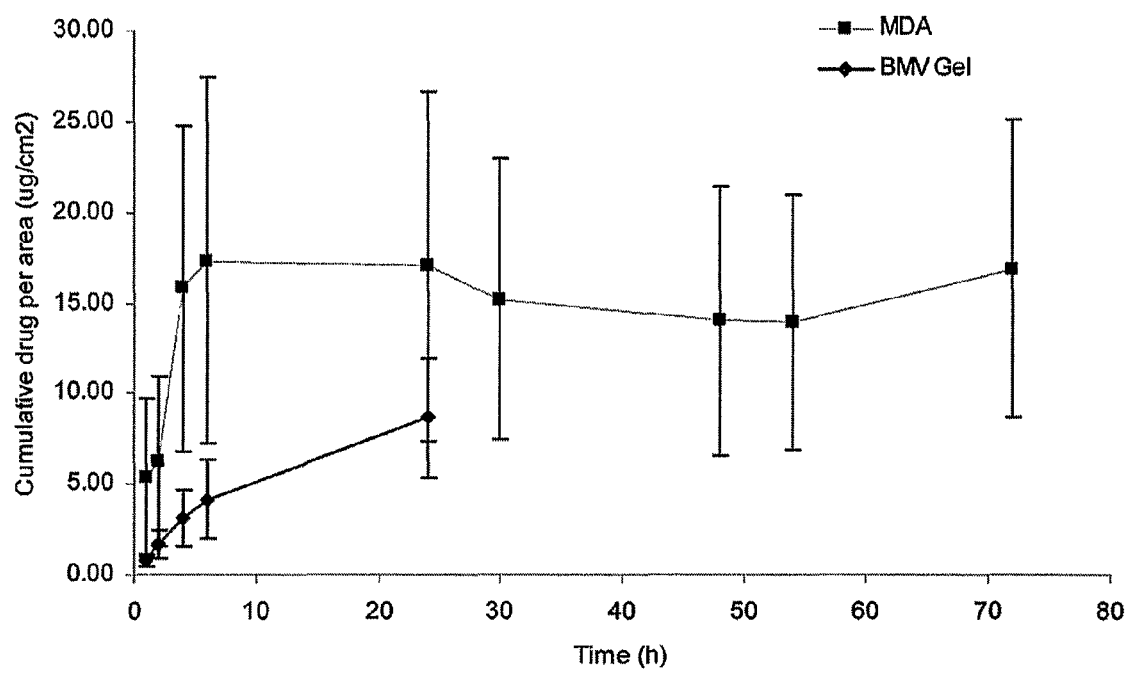

Administration of amounts of the 10% and 20% formulations such that the same amount of BDP is administered yield startlingly different uptake curves. The subsaturated 20% ethanol formulation exhibits a close relation with Fick's law for a time, before quickly plateauing off. It is likely that the HFA evaporates virtually immediately, and the ethanol evaporates at least until the solution is saturated, whereafter the flux is entirely as predicted by Fick's law. The ethanol will continue to evaporate, perhaps hindered by the PVP to a certain extent, and while any ethanol remains, the BDP will be saturated therein, but will not be present in solution at all, once the ethanol has evaporated, which is where the flux plateaus in the accompanying Figures, where the plateau indicates no further adsorption/permeation of membrane.

The saturated 10% ethanol formulation exhibits results that exceed those predicted by Fick's law i.e. where thermodynamic activity is equal to 1 and represented by the same drug dissolved in a non-volatile inert solvent e.g. poly(ethylene glycol), and which continue to show release for a period of time considerably in excess of that demonstrated by the subsaturated preparation. This cannot be accounted for by the initial preparation of, in this case, BDP in ethanol and PVP, as the only variation is in the final amount of HFA added, all other parameters being the same.

What is necessary is that the amount of drug in the formulation be a saturating amount, after addition of all of the components of the formulation, including the propellant. It does not matter whether a pre-mix, which is used herein to indicate a formulation of the invention lacking a propellant, is saturated, subsaturated, or even has undissolved drug present prior to addition of the propellant, provided that the final formulation is saturated for the drug, and that the formulation is monophasic.

Suitable solvents are generally selectable by those skilled in the art, and will be selected according to the drug chosen. Suitable solvents typically include; water, cyclomethicone, benzyl alcohol, propylene glycol, polyethylene glycol, propylene carbonate, ethanol, dimethyl sulphoxide, glycerin, isopropyl alcohol, isopropyl myristate, and oleic acid. Ethanol is particularly preferred, as it is capable of dissolving therapeutically useful amounts of most drugs suitable for topical administration, and it is a particular advantage of the present invention that considerably smaller amounts of ethanol need be used for any given drug, by comparison with the art. This has the advantage of reduced irritation, for example. The total amount of solvent in the formulation is not critical to the invention. However, ethanol and IPA may be present in amounts up to about 40%, while benzyl alcohol is restricted to a maximum of about 2.5% when HFA is used as propellant.

The pH of the formulation may be adjusted if desired, such as to assist in stability of the drug. In this respect, with BMV (betamethasone valerate) it has been found advantageous to reduce the pH to below 4 when ethanol is used as solvent, while no pH adjustment is necessary when IPA is used.

Formulations of the invention may also contain plasticisers for the purpose of delaying release of drug. In particular, plasticisers that do not readily evaporate, such as polymers, including PEG, are useful for this purpose. A combination of Eudragit and PVP has been shown to be useful for controlling drug release.

Surprisingly, the plasticiser may also serve to delay release of the drug from the film, while still permitting diffusion rates in excess of those predicted by Fick's law for a saturated solution of the drug. This effect can also lead to a longer period before total release across the membrane is finally equalled by a saturated solution under Fick's law.

The formulations of the invention are suitable for administration as aerosols or as solutions, for example. The high volatility of the propellant will generally require that the formulation be kept pressure-sealed, such as by a simple, manually operable valve for example, until use. Particularly useful dosage delivery devices are aerosol canisters, and the formulation may be sprayed or delivered by tube, for example. The formulation, after delivery, will tend to form a film, and the amount of film-forming agent and other excipients may be adjusted to determine whether the resulting film will be loose or tight, and whether the film may run before setting, or set straight away. These and settings inbetween may be adopted, as appropriate or desired.

For example, by manipulating the properties of the formulation, the actuated dose can be varied from a single aliquot of solution that forms a thick patch, to a fine aerosolised mist which covers a larger surface area.

It is a further advantage of the present invention that formulations of the invention can be manufactured safely without having to use combustible components, thereby reducing the costs associated with specialist equipment.

Other advantages include increasing the concentration of co-administrated penetration enhancers in the skin, thus reducing potential irritation/inflammation, and also in controlling the rapidity of release of the drug.

BRIEF DESCRIPTION OF THE DRAWINGS

FIG. 1 shows solubility data for BDP with 10% EtOH;

FIG. 2 shows BDP solutions consisting of 20% EtOH;

FIG. 3 shows solubility results for BMV in 10% EtOH;

FIG. 4 shows the diffusion of BDP through a synthetic membrane after the application of multiple shots of a saturated 10% EtOH BDP MDA spray;

FIG. 5 shows a direct comparison of BDP being released across a synthetic membrane from the 10% EtOH spray and a commercial BDP cream;

FIG. 6 is a comparison of BDP release across a synthetic membrane from two MDAs with varied amounts of ethanol (mean±standard deviation, n=5);

FIG. 7 shows a comparison of BMV release from a 10% EtOH BMV spray and marketed BMV cream using a synthetic membrane;

FIG. 8 is a comparison of 10% EtOH BMV spray and marketed product of BMV mousse;

FIG. 9 is a comparison of PVA:PVP MDA 10% EtOH spray and a drug saturated PEG solution;

FIG. 10 is a comparison of subsaturated, saturated and supersaturated BDP topical formulations;

FIG. 11 is a comparison of a saturated BDP topical MDA sprays containing various ratios of PVA and PVP with a non-volatile saturated PEG system and a 10% EtOH system without PEG;

FIG. 12 is a ternary phase plot of the BMV formulation at various excipient compositions;

FIG. 13 shows the mean cumulative amount of BMV released per unit area;

FIG. 13*a* shows the early part of release depicted in FIG. 13 and the gradients achieved in the first 0.8 hours;

FIG. 14 is a ternary phase plot of 2% salicylic acid at various excipient compositions;

FIG. 15 shows mean cumulative amount of BDP released per unit area (μg/cm2) over t=0.25-5 h from three novel spray formulations containing polyvinyl pyrrolidone, co-povidone and of Eudragit and PVP compared to a commercial comparator diprosone;

FIG. 16 is a ternary phase plot of benzoyl peroxide at various excipient compositions;

FIG. 17 shows the effect on the area of film by varying distance of the formulation from a filter paper;

FIG. 18 shows the effect on the area of the film with increase in the number of actuations of formulation; and FIG. 19 shows the mean cumulative amount of BMV permeating across the Stratum corneum per unit area (μg/cm2) during t=0.25-7 h from a novel spray formulation (MDA) compared to a gel (MV gel) comprising similar excipients except for the inclusion of hydrofluoroalkane propellant.

The invention will now be further illustrated with respect to the following, non-limiting Examples.

EXAMPLES

Materials and Methods:

The following materials and methods were used in the following Examples.

Materials:

| | Source |
|---|---|
| Materials | |
| Acetonitrile, HPLC Grade | Rathburn, Germany<br>BDH Laboratory Supplies, UK |
| Betnovate ® (betamethasone valerate cream), 0.01% w/w | GSK, UK |
| Betamethasone Dipropionate monohydrate BP, Micronized | Pharmaceutical Development Europe |
| Betamethasone Valerate BP, Micronized >99% purity | Symbiotec, India |
| Bettamousse ® (betamethasone valerate mousse), 0.01% w/w | Celltech, UK |
| Deionized Water | House Tap |
| Poly (ethylene glycol) 400 | BDH Laboratory Supplies, UK |
| Ethanol, 99.0-100.0% v/v | BDH Laboratory Supplies, UK |
| HPLC Vials 2 mL and Lids | VWR, UK |
| Metal Canisters | AstraZeneca, UK |
| Metal Canisters Valves | Valois, France |
| Parafilm | American National Can, USA |
| PET Canisters | AstraZeneca, UK |
| PET Canisters Valves | Valois, France |
| Plastipak plastic syringes | Becton Dickenson, UK |
| Poly(vinyl pyrrolidone) K30, MW 360,000 | Fluka, Switzerland |
| Poly(vinyl alcohol) 40% hydrolysed, MW, 72,000 | Polysciences Inc. USA |
| Regenerated Cellulose Acetate Dialysis Tubing (MWCO-12-14000 Daltons) | Medicell International, UK |
| Solkane ® 134a (HFA) | Solvay, UK |
| Apparatus | |
| 717 Plus Autosampler | Waters, UK |
| 996 Photodiode Array Detector | Waters, UK |
| Ace 5 $C_{18}$ 150 mm × 4 μm HPLC Column | Hichrom Limited, UK |
| Analytical Balance | Sartorious, Germany |
| Analytical Balance AT200 | Mettler Toledo, UK |
| Filter Unit | Sartorious, Germany |
| Franz Cells | Medpharm, UK |
| Gilson pipette | Pipetman, France |
| Hand Operated Laboratory Plant, Type 2016 | Pamasol Willi Mader AG, Switzerland |
| Hot plate | Fisons, UK |
| Magnetic Followers 13 mm, PTFE | Cowie Technology, UK |
| Novapak ® $C_{18}$ 150 mm × 4 μm HPLC Column | Waters, Ireland |
| Stir plate, 15 points | H + P Labortechnik AG, Germany |
| Volumetric Flasks and beakers | Fisher, UK |
| Water bath heater and stirrer | Grant Instruments, UK |

Methods:

Solubility Studies:

Solubility studies were conducted in clear, PET canisters. Stir bars were added to the canister and the canister was tared on an analytical balance. Beclomethasone dipropionate (BDP) or beclomethasone valereate (BMV), poly(vinyl pyrrolidone) (PVP) and the plasticizer (e.g. poly (ethylene glycol) (PEG), if required) was added to the vials. Either 10% or 20% ethanol (EtOH) was added by weight via a Gilson pipette. Lids were placed on the canisters and crimped. The solutions were left to stir overnight. The HFA was added the next day and the clarity of the solution was observed. The solutions were left to stir or sit for several days as needed, to check for improved transparency or precipitation. The results were plotted on a ternary phase plot to find the boundary for saturated solutions. Only saturated solutions were utilised in the subsequent experiments. All percentages are based on weight/weight calculations.

Release Studies:

The release experiments were carried out in upright Franz cells, with an average volume of 10.8 $cm^3$. Regenerated cellulose acetate dialysis tubing soaked in deionised $H_20$ for up to one hour at 70° C. and then rinsed with deionised $H_20$ to remove any impurities was used to model a synthetic membrane. The membrane was then cut to fit the Franz cells with scissors and placed in the Franz cell with a magnetic flea in the bottom half. The top of the cell was positioned over the membrane and the cell was fully assembled by wrapping parafilm around the two sections to ensure no leaks occurred. The cell was then inverted, filled immediately with 70:30 acetonitrile (ACN):$H_20$, and placed in a pre-heated water bath at 37° C. with a submerged stir plate. This system was left to equilibrate for half an hour. To ensure there was no contamination of the cells, a zero time point was taken prior to any application of formulations. The remaining time points were 15 min, 30 min, 45 min, 60 min, 90 min, 2 h, 3 h, and 4 h. The 1 mL samples were taken out of the sampling arm of the cell, placed directly in to an HPLC vial, and replaced with 1 mL of receiver fluid that was kept at the same temperature in the water bath.

The formulations were made up within aluminium canisters and crimped with a metered dose lid (containing a dip tube) as described in the solubility studies. Ten shots from the canisters were sprayed to waste in order to prime the nozzle for an accurate application. The canister was then weighed. The appropriate numbers of shots were applied to the cell and the canister was reweighed to check for the amount of the formulation that was discharged. Five Franz cells were used to test each formulation. All Franz cells were left unoccluded in the study. In the case of the marketed creams, a 5 mL plastic syringe was disassembled and filled with the cream. One mL of cream was applied to each cell, and then one mL of the cream was weighed to calculate the percentage of BDP applied. For the BMV mousse, the canister was weighed before and after application to the Franz cell, and the nozzle was pressed for approximately one second to discharge the mousse into the cell.

Drug Recovery:

Samples taken from the Franz cells were assayed by high pressure liquid chromatography (HPLC). The HPLC conditions for BDP were as follows:

| | |
|---|---|
| Column | Novapak ® $C_{18}$ 150 mm × 4 μm HPLC Column |
| Column Temperature | Ambient |
| Mobile Phase | 70:30 ACN:$H_20$ |
| Flow Rate | 1.0 mL/min |
| Injection Volume | 100 μL |
| UV Wavelength | 254 nm |
| Run Time | 6 min |

The HPLC conditions for BMV were as follows:

| Column | Ace 5 $C_{18}$ 150 mm × 4 µm HPLC Column |
| --- | --- |
| Column Temperature | Ambient |
| Mobile Phase | 70:30 ACN:$H_2O$ |
| Flow Rate | 1.0 mL/min |
| Injection Volume | 10 µL |
| UV Wavelength | 239 nm |
| Run Time | 6 min |

Both methods were validated for stability and accuracy. Results were calculated by comparing either the sample peak area (for BDP) or the sample peak height (for BMV) to the y=mx+b calibration curve from a series of five standards. A correction factor was utilised to account for the one mL samples taken from the receiver chamber. The cumulative amounts of drug in the receiver chamber were plotted against time and the flux, J, was calculated from the slope of that curve.

Example 1

The Production of BDP, 10% EtOH, HFA Solution Formulations

FIG. 1 is a ternary diagram displaying the phase behaviour of BDP metered dose aerosol (MDA) solution formulations containing 10% EtOH.

The maximum amount of BDP that is soluble is never more than about 1%, and that amount decreases rapidly as more than 2% PVP is added.

Example 2

The Production of BDP, 20% EtOH, HFA Solution Formulations

Figure 2:
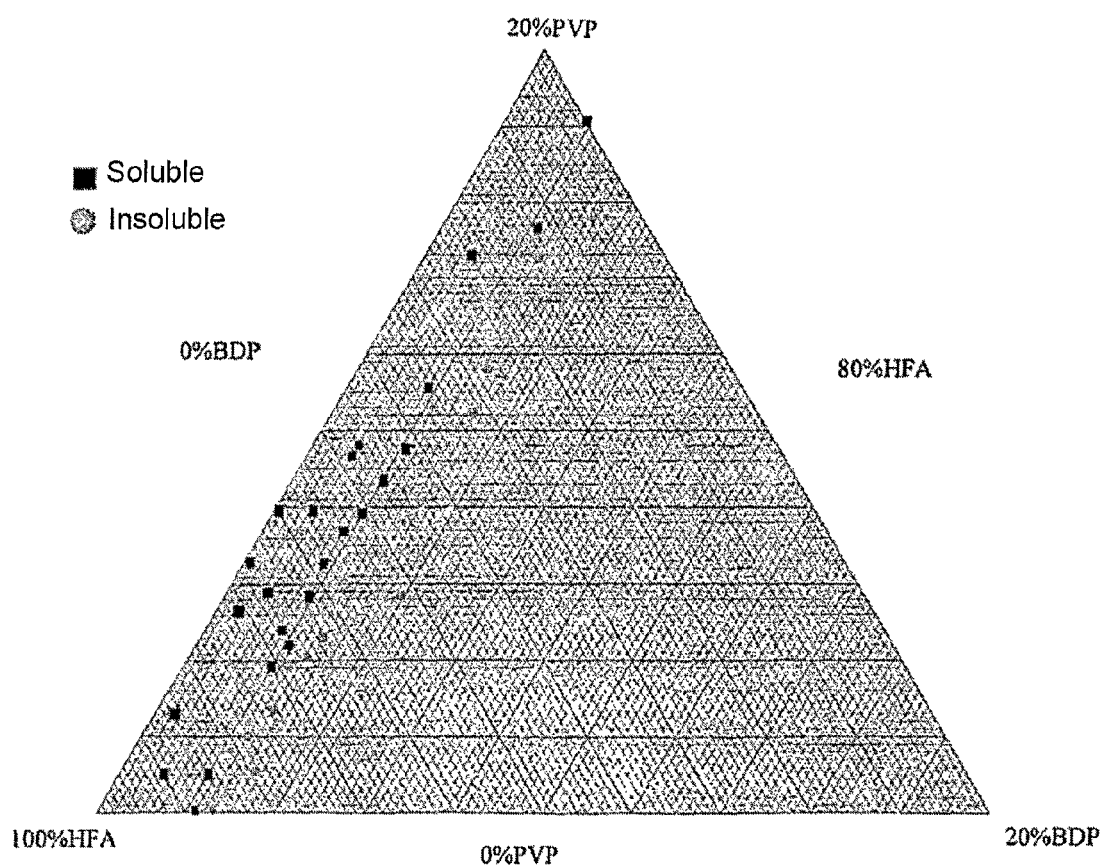

FIG. 2 is a ternary diagram displaying the phase behaviour of BDP metered dose aerosol (MDA) solution formulations containing 20% EtOH.

The maximum solubility for this system is about 2.2% BDP all the way through to 18% PVP. Higher amounts of PVP were not investigated as the addition of high quantities of polymer increased the viscosity to such a degree that the formulation could not be dosed effectively. Doubling the percentage of EtOH in the system more than doubled the solubility of BDP implying a complex relationship between the formulation components.

Example 3

The Production of BMV, 10% EtOH, HFA Solution Formulations

Figure 3:
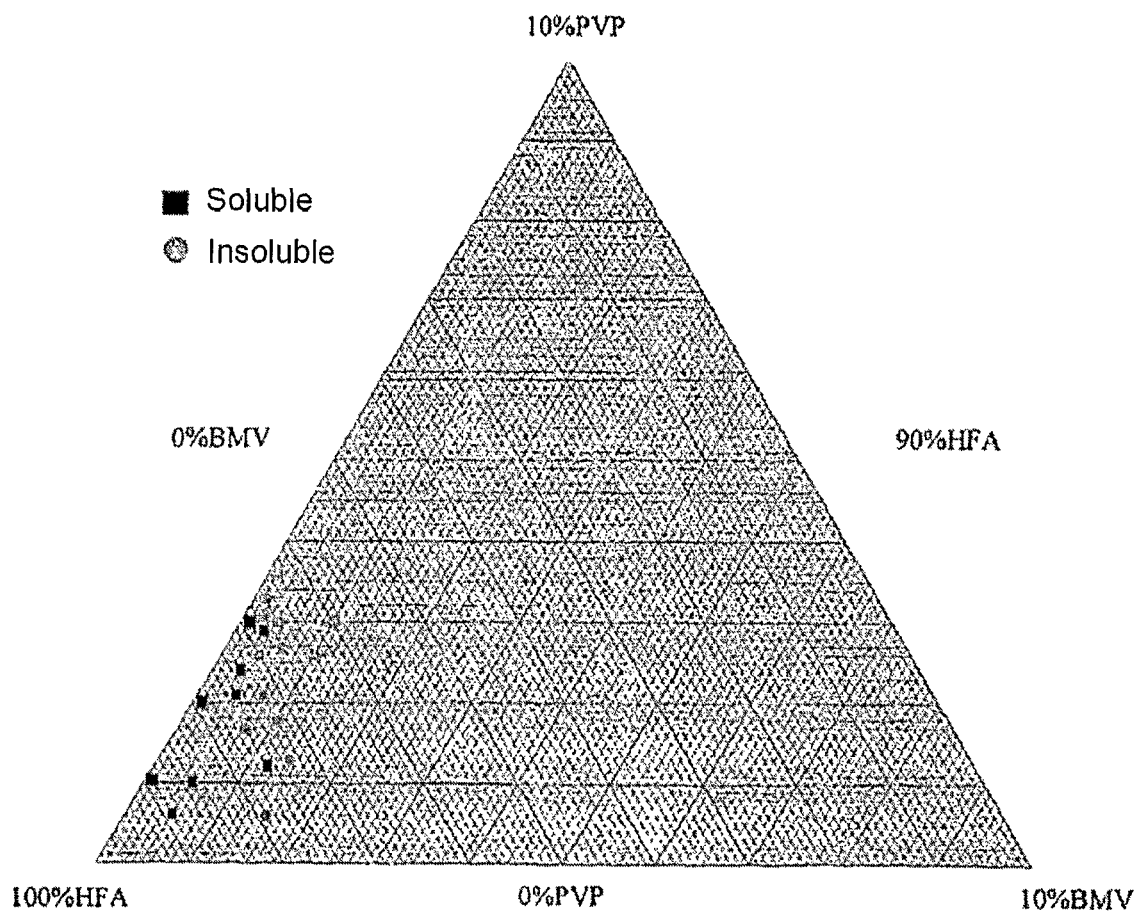

FIG. 3 is a ternary diagram displaying the phase behaviour of BDP metered dose aerosol (MDA) solution formulations containing 20% EtOH.

These results are similar to the BDP in 10% EtOH, where the drug becomes insoluble at around 3% PVP. Both systems also seem to have a maximum solubility at 1-1.2% drug.

Example 4

The Solubility of BDP in a 10% EtOH, PVP, HFA Solution with Water Added as a Plasticiser The compatibility of water with the BDP, EtOH, PVP, HFA solutions was tested and the results are shown in table 2. All numbers are % w/w with all components, i.e. including EtOH.

TABLE 2

Compatibility of 10% EtOH, BDP, HFA, PVP and water within a metered dose aerosol (MDA) formulation.

| Components | Formulation 1 (%) | Formulation 2 (%) | Formulation 3 (%) | Formulation (%) 4 |
| --- | --- | --- | --- | --- |
| PVP | 1.1 | 99.5 | 1.1 | — |
| BDP | 0.3 | — | 0.1 | — |
| EtOH | 10.5 | — | 10.6 | 9.3 |
| $H_2O$ | 1.3 | 0.5 | 0.2 | 0.9 |
| HFA | 86.8 | — | 88.0 | 89.8 |
| Result | Insoluble | Soluble | Soluble | Soluble |

The solubility of the components in the ethanol/HFA mixture was determined visually. As detailed in table 2, up to 0.9% water was soluble within the MDA compositions but the composition containing 1.3% water did not produce a single phase system.

Example 5

The Diffusion of BDP from a 10% EtOH, PVP, HFA Solution

The 10% EtOH, BDP, HFA, PVP MDA formulation composition is shown in table 3:

TABLE 3

10% EtOH, BDP, HFA, PVP formulation composition

| Excipient | Formulation | Description |
| --- | --- | --- |
| PVP | 2.46% | 2.7% |
| BDP | 0.09% | 0.1% |
| EtOH | 9.83% | — |
| HFA | 87.62% | 97.2% | where the "formulation" is the actual percentages of the excipients in the canister, and the "description" is utilised to find the saturation level illustrated in FIG. 1. This formula was used for the generation of the experimental results displayed in FIG. 4.

Figure 4:
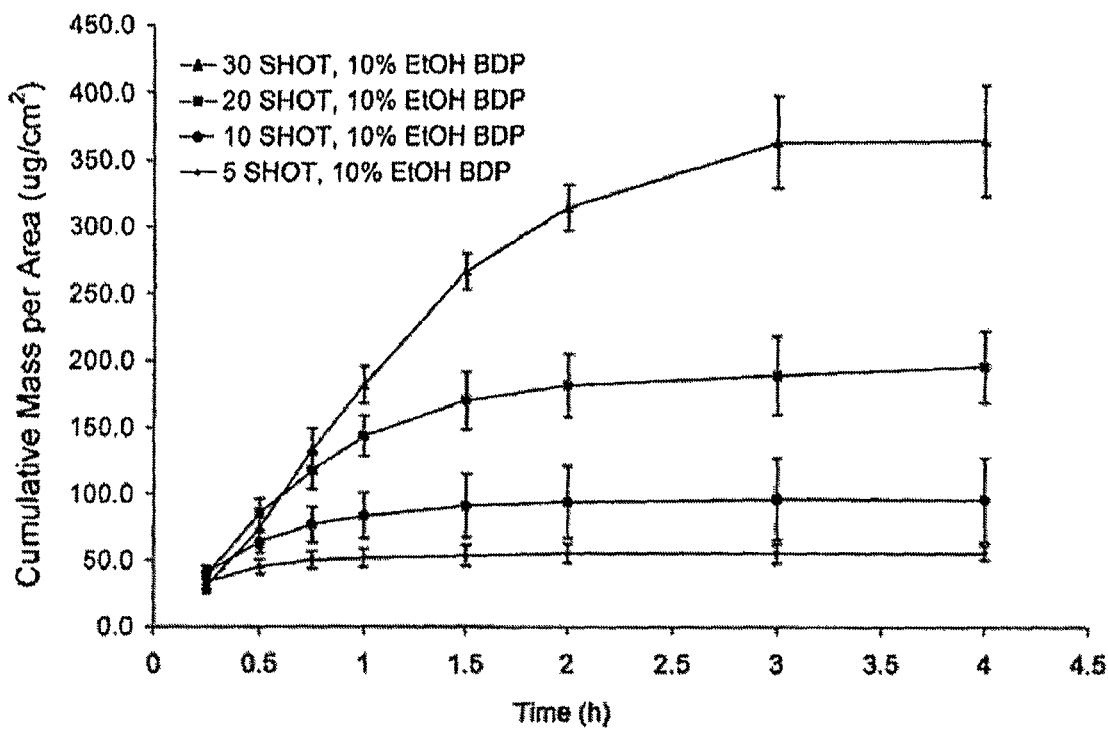

FIG. 4 shows the diffusion of BDP through a synthetic membrane after the application of multiple shots of a saturated 10% EtOH BDP MDA spray (mean±standard deviation, n=5).

The total cumulative mass of the drug per $cm^2$ released from the Spray formulations after 4 h are roughly proportional to the number of shots: 5, 10, 20, and 30 shots resulted in an average cumulative masses of 55.7, 95.7, 195.6, and 364.3 µg/cm2 respectively. At each of the time points after the 60 min all of the drug concentrations displayed on FIG. 4 are significantly different from each other. These results demonstrate that the total amount of BDP released from the formulation is dependent upon the number of shots i.e. the quantity of formulation applied to the membrane. However, the flux of the 20 and 30 sprays was very similar during the first few time points on the release profile which indicates that for these the rate of release is not dependant on the quantity of formulation applied. Applying a greater amount of sprays simply prolongs the time that steady state diffusion occurs making measurement of the diffusion rate at equilibrium easier.

Example 6

Comparison of the BDP Diffusion from a 10% EtOH, HFA Solution to an Equivalent Commercial BDP Cream The 10% EtOH, BDP, HFA, PVP formulation composition is shown in table 4:

TABLE 4

| 10% EtOH, BDP, HFA, PVP formulation composition: | | |
|---|---|---|
| Excipient | Formulation | Description |
| PVP | 2.46% | 2.7% |
| BDP | 0.09% | 0.1% |
| EtOH | 9.83% | — |
| HFA | 87.62% | 97.2% |

Where the "formulation" is the actual percentages of the excipients in the canister, and the "description" is utilised to find the saturation level illustrated in FIG. 1.

Figure 5:
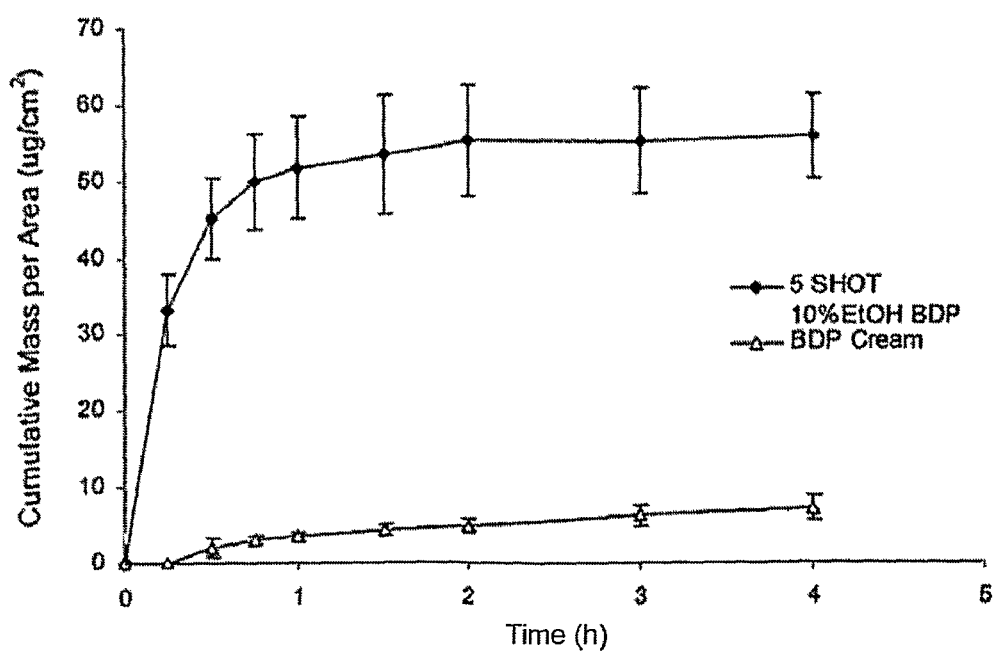

FIG. 5 is a comparison of BDP release from a 10% EtOH BDP MDA spray and a marketed cream containing using a synthetic membrane (mean±standard deviation, n=5).

Five shots of the spray were required to reach a similar concentration in the Franz cell to one mL of BDP cream. The average amount of BDP in the donor cell was 210 μg for the spray and 222 μg for the cream. At each of the time points taken the quantity of drug released across the membrane by the spray was significantly greater compared to the cream ($p<0.05$, ANOVA). In addition, the flux of the BDP cream was 1.7 $\mu g/cm^2/h$ and the flux of the BDP spray was 33.8 $\mu g/cm^2/h$. As the spray released the BDP across the membrane at a rate that was over 20 times faster than the cream this implies that the spray would be far more efficient in delivering BDP to the skin compared to the commercial preparation.

Example 7

The Effects of EtOH Concentration in the BDP, HFA, EtOH, PVP Solution

Table 5 and 6 detail the formulations that were used to compare the effect of EtOH on the release of BDP where the "formulation" is the actual percentages of the excipients in the canister, and the "description" is utilised to find the saturation level illustrated in FIGS. 1 and 2 respectively:

TABLE 5

| 10% EtOH, BDP, HFA, PVP formulation composition: | | |
|---|---|---|
| Excipient | Formulation | Description |
| PVP | 1.85% | 2.1% |
| BDP | 1.02% | 1.1% |
| EtOH | 10.31% | — |
| HFA | 86.83% | 96.8% |

TABLE 6

| 20% EtOH, BDP, HFA, PVP formulation composition | | |
|---|---|---|
| Excipient | Formulation | Description |
| PVP | 3.30% | 4.2% |
| BDP | 1.81% | 2.3% |
| EtOH | 20.60% | — |
| HFA | 74.28% | 93.5% |

Figure 6:
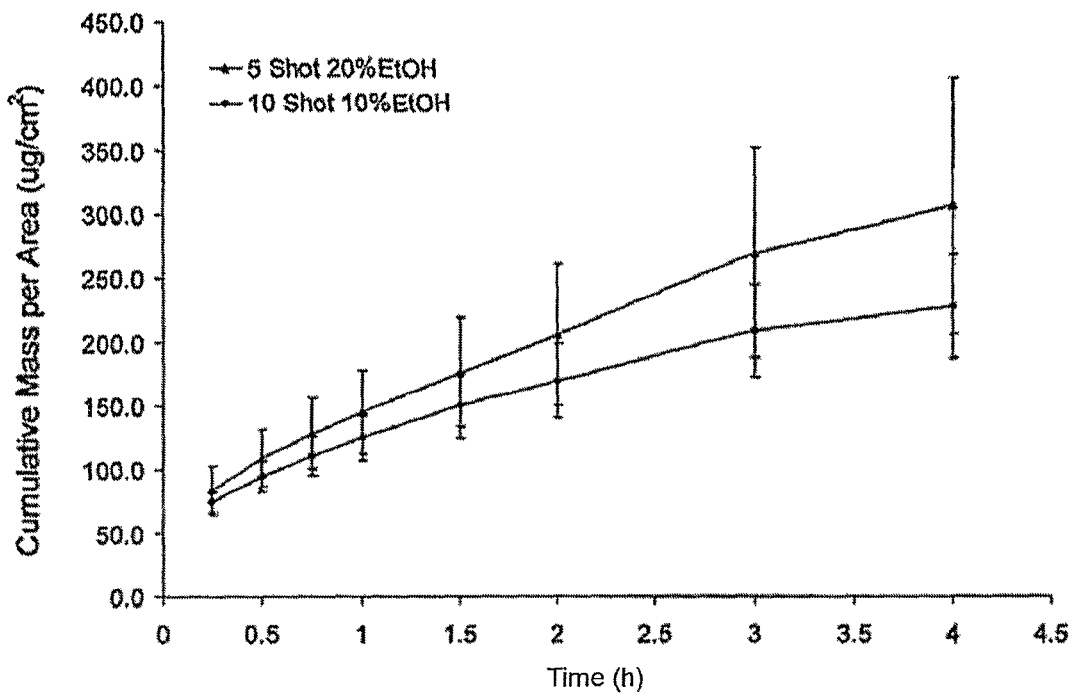
Figure 7:
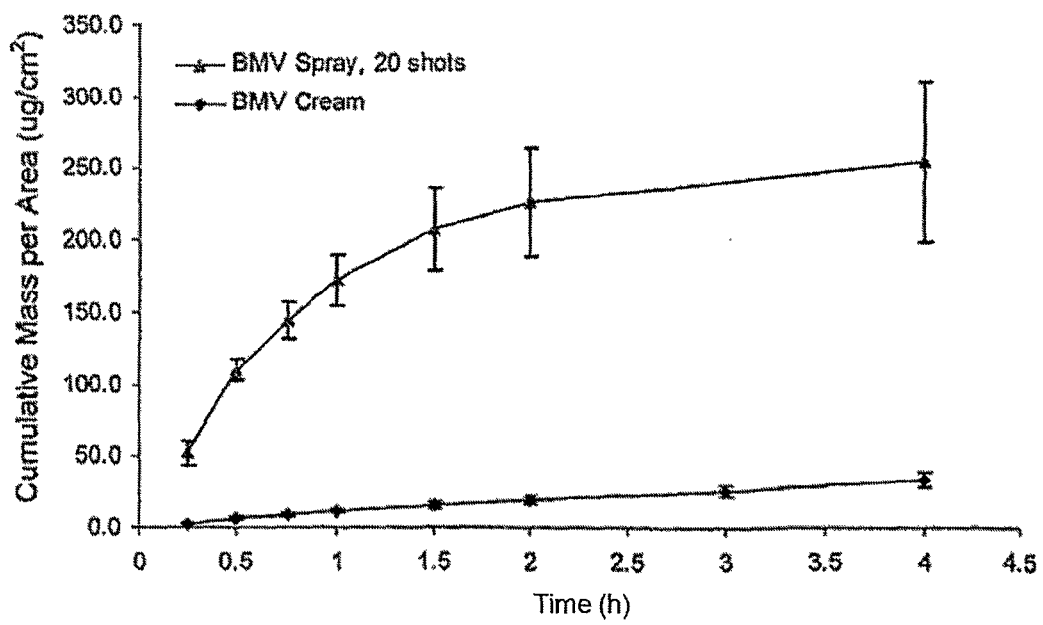
Figure 8:
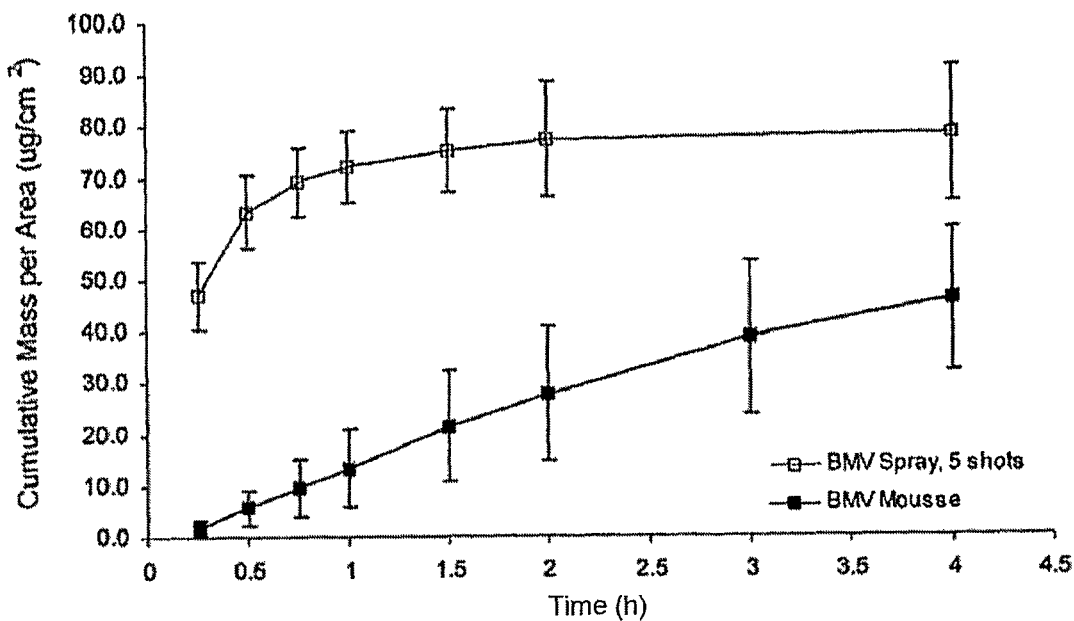

FIG. 6 is a comparison of the BDP release across a synthetic membrane from two MDAs with varied amounts of ethanol (mean±standard deviation, n=5). The average amount of the 20% EtOH formulation applied to the Franz cells was 4735.2 μg. The average amount of the 10% EtOH formulation applied was 4045.0 μg. However, as displayed in FIG. 6 there was no significant difference ($p>0.05$, ANOVA) in the concentration of BDP released from the formulation containing 10% EtOH compared to the formulation containing 20% EtOH. This indicates that the saturated solubility of the drug in the vehicle has no obvious effect on the flux from this type of formulation.

Example 8

Figure 9:
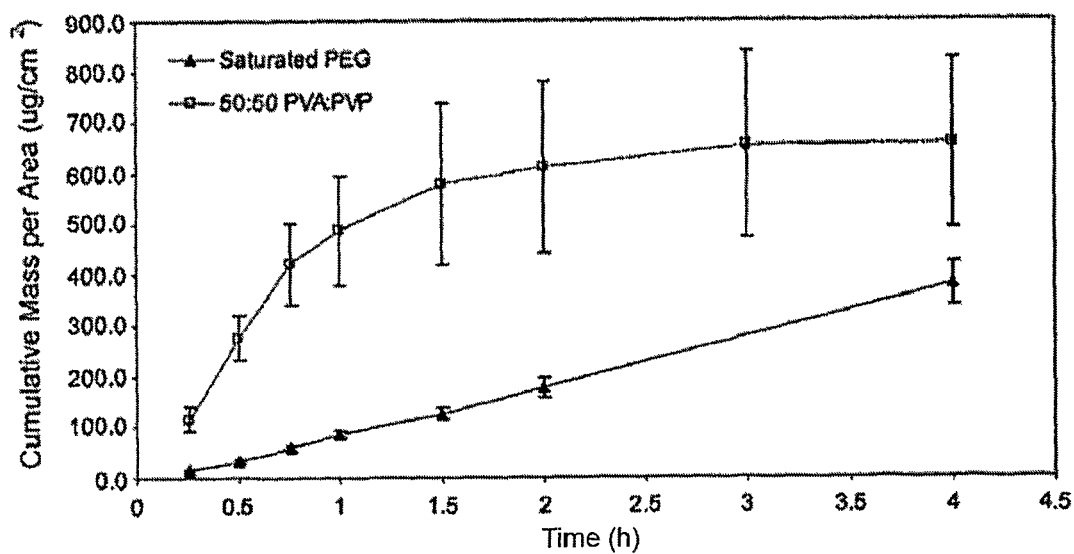

Release of BMV from a HFA, EtOH, PVP Solution in Comparison to Two Commercial Products The 10% EtOH BMV spray (table 7) was compared to two marketed products containing BMV: a cream and a mousse. A different number of shots of the same spray were necessary to compare to these two different marketed formulations. The formulation used for both comparisons is displayed in Table 7 where the "formulation" is the actual percentages of the excipients in the canister, and the "description" is utilised to find the saturation level illustrated in FIG. 3.

TABLE 7

| 10% EtOH, BMV, HFA, PVP formulation composition: | | |
|---|---|---|
| Excipient | Formulation | Description |
| PVP | 2.40% | 2.7% |
| BMV | 0.10% | 0.1% |
| EtOH | 9.26% | — |
| HFA | 88.24% | 97.2% |

Twenty shots of the spray were required for comparison with the BMV marketed cream; five shots were needed to compare to the BMV marketed mousse.

FIG. 7 shows a comparison of BMV release from a 10% EtOH BMV spray and marketed BMV cream using a synthetic membrane (mean±standard deviation, n=5).

The average amount of BMV in the spray applied in the Franz cell was 965 μg and the average amount of BMV in the cream was 938 μg. At all of the time points show in FIG. 7 the HFA spray released a significantly larger ($p<0.05$, ANOVA) concentration of BMV across the synthetic membrane compared to the commercial cream. The flux of the BMV spray was 158.4 $\mu g/cm^2/h$ while the flux of the BMV marketed cream was 8.4 $\mu g/cm^2/h$. Thus, the HFA formulation was again over 15 times more efficient in releasing BMV across the synthetic membrane compared to the commercial cream.

FIG. 8 is a comparison of 10% EtOH BMV spray and marketed product of BMV mousse (mean±standard deviation, n=5).

Five shots of the BMV spray resulted in 250 μg applied to the Franz cell. The "1 second" depression of the mousse dose release valve produced on average 240 μg of BMV. At all of the time points show in FIG. 9 the HFA spray released a significantly larger (p<0.05) concentration of BMV across the synthetic membrane compared to the commercial cream.

The flux of the BMV spray was 44.2 µg/cm$^2$/h and the flux of the BMV mousse was 14.8 µg/cm$^2$/h. Thus, the BMV spray was releasing the BMV across the membrane at twice the rate as the mousse but with 20% of the EtOH content.

Example 9

The effects of adding a Plastisizer PVA to the BDP, HFA, EtOH, PVP Solution

The release of BDP from a drug saturated PEG solution (table 8) was compared to a 10% EtOH, HFA MDA containing PVP, PVA 40% and saturated BDP, hydrolysed (table 9).

TABLE 8

Drug saturated formulation composition:

| Excipient | Saturated (%) |
| --- | --- |
| PEG 400 | 92.04 |
| BDP | 7.96 |

TABLE 9

10% EtOH, BDP, HFA, PVP and PVA 40% hydrolysed formulation composition:

| Components | Formulation (%) |
| --- | --- |
| PVP | 1.3 |
| BDP | 0.9 |
| EtOH | 15.0 |
| PVA | 1.2 |
| HFA | 81.6 |

FIG. 9 is a comparison of PVA:PVP MDA 10% EtOH spray and a drug saturated PEG solution (mean±standard deviation, n=5).

In both cases an 'infinite' dose was applied to the membrane held in a diffusion cell and the rate of diffusion from the saturated PEG solution was 89.11 µg/cm$^2$/h (taken from the first five points) compared to 503.10 µg/cm$^2$/h (taken from the first 4 data points).

Example 10

The Flux of a Drug Saturated Volatile Spray Vs a Non Volatile Saturated and Subsaturated System The compositions of the formulations used in this experiment are detailed in Tables 10 and 11 where the "formulation" is the actual percentages of the excipients in the canister, and the "description" is utilised to find the saturation level illustrated in FIGS. 2 and 3.

TABLE 10

Drug supersaturated and subsaturated novel Spray formulation compositions:

| Excipient | Saturated volatile Formulation (%) | Saturated volatile Description (%) | Subsaturated Formulation (%) | Subsaturated Description (%) |
| --- | --- | --- | --- | --- |
| PVP | 2.46 | 2.7 | 3.2 | 4.03 |
| BDP | 0.09 | 0.1 | 0.2 | 0.20 |
| EtOH | 9.83 | — | 20.5 | — |
| HFA | 87.62 | 97.2 | 77.7 | 76.1 |

TABLE 11

Drug saturated solution formulation composition:

| Excipient | Saturated non-volatile(%) |
| --- | --- |
| PEG 400 | 92.04 |
| BDP | 7.96 |

Figure 10:
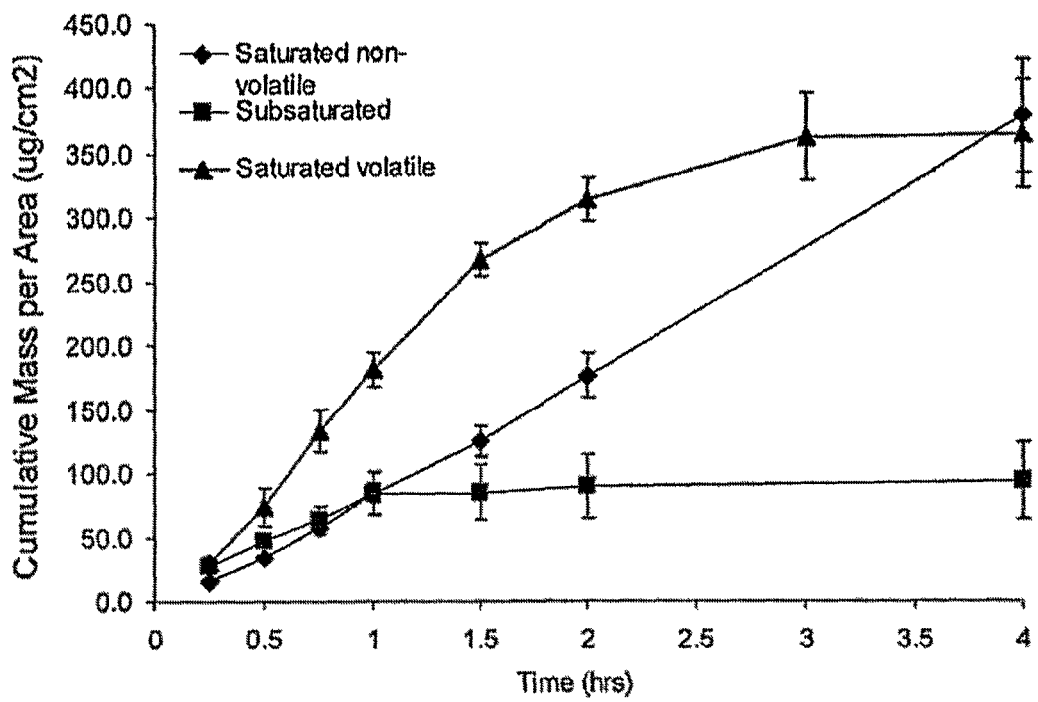

FIG. 10 is a comparison of subsaturated, saturated and supersaturated BDP topical formulations (mean±standard deviation, n=5).

After 15 min each of the three formulations allows the diffusion of approximately the same quantity of drug through the membrane. However, after 60 min the Saturated volatile system has allowed over double the quantity of BDP across the membrane compared to the other two formulations.

The flux of BDP from the subsaturated system was calculated to be 63.62 µg/cm$^2$/h, the non-volatile saturated system 89.10 µg/cm$^2$/h and the volatile saturated system 206.08 µg/cm$^2$/h. Thus, the rate of drug diffusion from the saturated volatile formulation was far superior to both the non-volatile saturated and subsaturated topical formulations. This indicates the importance of formulating the MDA as a saturated system prior to dose administration.

Example 11

The Effects of Adding a Plasticiser PEG 400 to the BDP, HFA, EtOH, PVP Solution

The compositions of the formulations used in this experiment are detailed in Tables 12 and 13 where (if appropriate) the "formulation" is the actual percentages of the excipients in the canister, and the "description" is utilised to find the saturation level illustrated in FIG. 1.

TABLE 12

Drug saturated volatile formulation compositions:

| Excipient | 10% EtOH no plastic formulation (%) | 10% EtOH no plastic description (%) | 5% PEG formulation (%) |
| --- | --- | --- | --- |
| PVP | 2.5 | 2.7 | 2.6 |
| BDP | 0.1 | 0.1 | 0.1 |
| PEG 400 | — | — | 4.5 |
| EtOH | 9.7 | — | 9.1 |
| HFA | 87.7 | 97.2 | 83.7 |

TABLE 13

Drug saturated non-volatile and drug saturated volatile formulation compositions:

| Excipient | 10% PEG formulation (%) | Saturated PEG (%) |
|---|---|---|
| PVP | 3.0 | — |
| BDP | 0.1 | 7.96 |
| PEG 400 | 10.1 | 92.04 |
| EtOH | 10.1 | — |
| HFA | 76.7 | — |

Figure 11:
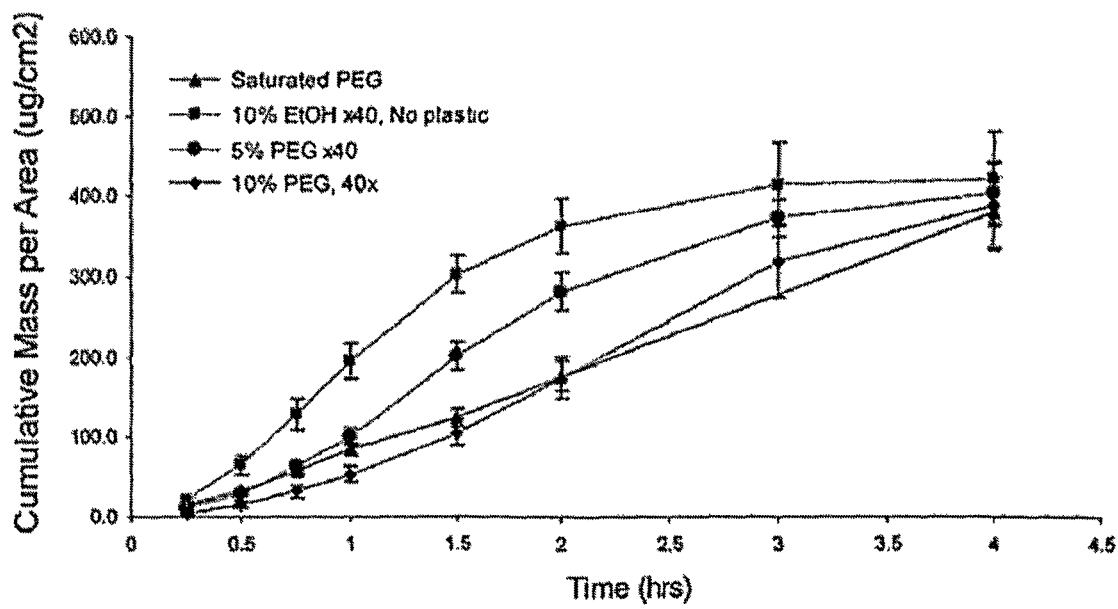

FIG. 11 is a comparison of a saturated BDP topical MDA sprays containing various ratios of PVA and PVP with a non volatile saturated PEG system and a 10% EtOH system without PEG (mean±standard deviation, n=5).

After 15 min each of the three formulations allows the diffusion of approximately the same quantity of drug through the membrane. However, after 60 min the Saturated volatile system without a plasticiser has allowed over double the quantity of BDP across the membrane compared to the drug saturated PEG system. Adding an increasing quantity of PEG to the ethanol, PVP, BDP, HFA volatile systems reduced the rate at which the BDP diffused through the membrane but, also increased the time to 'dose depletion' in the system i.e. the drug flux remained constant (without the graph plateauing) for a longer period of time.

The flux of BDP from the non-volatile saturated system was 89.10 µg/cm$^2$/h, from the 10% PEG formulation it was 82.57 µg/cm$^2$/h, 5% PEG formulation it was 155.17 µg/cm$^2$/h and the volatile saturated system 230.44 µg/cm$^2$/h. Thus, the rate of drug diffusion from the saturated volatile formulations could be manipulated using a plasticiser. The time to 'dose depletion' was >4 h for the non volatile saturated system, 4 h for the 10% PEG system, 3 h for the 5% PEG system and only 2 h for the MDA without at plasticiser (FIG. 11).

Examples 12-20

Materials and Methods
The following were used in the Examples 12-20.
Materials:

| Materials | Source |
|---|---|
| Acetonitrile, HPLC Grade | Rathburn, Germany |
| Deionised Water | BDH Laboratory Supplies, UK |
| | House Tap |
| Betamethasone Dipropionate monohydrate BP, Micronised | Pharmaceutical Development Europe |
| Betamethasone Valerate BP, Micronised >99% purity | Symbiotec, India |
| Polyvinyl pyrollidone K90 (Plasdone ® K90), USP grade - | ISP, Switzerland |
| Ammonia methacrylate co-polymer (Eudragit RSPO), Ph. Eur and NF grade - | Degussa, Germany |
| Co-povidone K-25-30 (Plasdone ® S-630), USP and Ph. Eur grade | ISP, Switzerland |
| Isopropyl alcohol | Fisher, UK |
| Ethanol, 99.0-100.0% v/v | BDH Laboratory Supplies, UK |
| HPLC Vials 2 mL and Lids | VWR, UK |
| Metal Canisters | AstraZeneca, UK |
| Metal Canisters Valves | Valois, France |
| Parafilm | American National Can, USA |
| Schott Canisters | AstraZeneca, UK |
| Metering Valves | Valois, France |
| Plastipak plastic syringes | Becton Dickinson, UK |
| Hydrochloric acid | Sigma, UK |
| Regenerated Cellulose Acetate Dialysis Tubing (MWCO-12-14000 Daltons) | Medicell International, UK |
| Hydrofluoroalkane (HFA) Solkane ® 134a | Solvay, UK |
| Brij 98 | Sigma, UK |

Methods
Definition of a Supersaturated System

In order to maintain the polymer and drug ratio constant and thus isolate the effects of drug saturation, the proportion of co-povidone (the antinucleating agent) and BMV was fixed at a ratio of 2:1 whilst the percentage of HFA varied. A series of three formulations (Table 14) that follow the tie line displayed in FIG. 12 were manufactured, assessed for precipitation and prepared for the release study if found to be monophasic.

Figure 12:
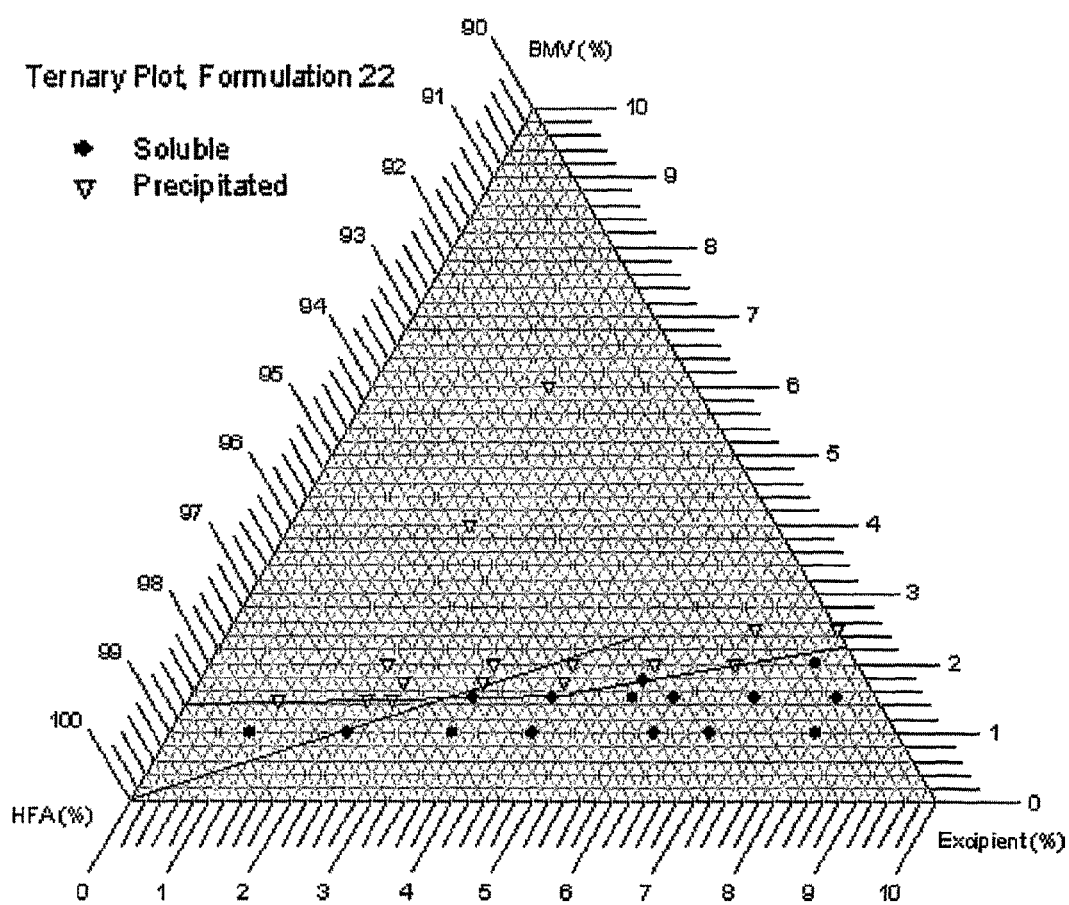

Accompanying FIG. 12 is a ternary phase plot of the BMV formulation at various excipient compositions. The phase boundary is shown between the 'soluble' and 'precipitated' points. A tie line (steeper, and starting in the bottom left) illustrates where the formulations would have a consistent co-povidone:BMV concentration but, different saturation states.

TABLE 14

Composition of BMV formulations used in the release study. Actual represents the weights of components weighed into the formulation whilst theoretical represents the theoretical ratio aimed for and for plotting on a ternary phase plot.

| | Actual % in formulations | | | | Theoretical % (Ternary phase) | | |
|---|---|---|---|---|---|---|---|
| Formulation | S-630 Copovidone | BMV | Ethanol | HFA | S-630 Copovidone | BMV | HFA |
| 1.00% BMV | 2.000 | 1.000 | 10.000 | 87.000 | 2.222 | 1.111 | 96.667 |
| 0.50% BMV | 1.000 | 0.500 | 10.000 | 88.500 | 1.111 | 0.556 | 98.333 |
| 0.13% BMV | 0.025 | 0.013 | 10.000 | 89.963 | 0.028 | 0.014 | 99.958 |

A saturated solution of BMV in ethanol was also prepared by adding excess BMV into a 100% ethanol. Any excess drug was filtered through a 0.2 μm syringe filter and the resultant filtrate used as a saturated BMV solution in ethanol.

The release experiments were carried out in upright Franz cells, with an average receiver compartment volume of approx. 11 ml. Regenerated cellulose acetate dialysis tubing soaked in deionised $H_2O$ for up to 1 h at 70° C. and then rinsed with deionised $H_2O$ to remove any impurities was used to model a synthetic membrane. The membrane was then cut to fit the Franz cells with scissors and placed between the donor and receiver compartment of the cell with a PTFE magnetic stirrer bar in the receiver section. The cell was secured together by using Parafilm around the two sections to ensure no leaks occurred. The cell was then inverted, filled immediately with 20% ethanol, 2% Brij 98 in phosphate buffered saline (PBS), and placed in a pre-heated water bath at 32° C. on a submerged stir plate. This system was left to equilibrate for approx. 30 min. To ensure there was no contamination of the cells, a t=0 time point was taken prior to any application of formulations. The 0.5 mL samples were removed from the sampling arm of the cell, assayed directly via HPLC, and replaced with 0.5 mL of receiver fluid previously maintained at the same temperature.

The metered dose aerosol formulations were prepared in PET coated glass canisters and crimped with a metered dose valve (containing a dip tube). Ten actuations from each canister were actuated to waste in order to prime the nozzle for accurate application. The canister was then weighed. Fifty actuations were applied to the donor compartment of each cell and the canister was reweighed to determine for the amount of the formulation actuated. The saturated ethanol solution was constituted and 1 ml placed in the donor compartment of the Franz cells. All Franz cells were left un-occluded in the study.

Drug Stability Studies

Ethanol was acidified by the drop wise addition of hydrochloric acid (HC1, 1 M) until a pH of approx. 3.5 was reached. The formulations were prepared by the sequential weighing of BMV, followed by excipients and ethanol into each canister. The canisters were shaken for 16 h prior to the addition of HFA (Table 15). The formulations were stored at 25° C. and samples removed at t=0 and t=4 weeks using an in-house device. The drug concentration in each of the preparations was assessed by extraction into ethanol prior to assay by HPLC. The concentration of drug was compared to the theoretical concentration delivered by a homogeneous formulation to calculate the relative % drug in the formulations.

TABLE 15

Compositions of the formulations to assess the stability of the metered dose aerosol formulations.

| Formulation | BMV | IPA | Ethanol pH 3.5 | Copovidone S-630 | HFA |
|---|---|---|---|---|---|
| BMV with ethanol | 0.05% | — | 10.00% | — | 89.95% |
| BMV with IPA | 0.05% | 10.00% | — | 3.00% | 86.96% |
| BMV with acidified ethanol | 0.05% | — | 10.00% | 3.00% | 86.95% |

BMV—betamethasone valerate,
IPA—isopropyl alcohol, HFA.

BMV Phase Diagram Construction

Formulations were prepared by the sequential weighing of the drug followed by the remaining excipients into a 10 mL PET glass coated canister. A magnetic stirrer bar was added and the formulations were crimped with a 100 μL valve. The formulations were allowed to shake for approximately 16 h at room temperature prior to the addition of HFA, and then shaken for a further 8 h prior to visual solubility assessment.

The Effect of Polymer on the Release Rate of Betamethasone Dipropionate

The formulations were prepared by the sequential weighing of betamethasone dipropionate (BMDP), excipient(s) and ethanol into a 10 mL PET coated glass canister. A PTFE-coated magnetic follower was added to each canister and sealed with a crimp top valve. The BMDP and excipient were allowed to hydrate in the ethanol while being vigorously shaken on a bench top shaker at room temperature for approximately 12 h. Following this, the required amount of HFA was added and the formulations left shaking for a further 1 h (Table 16).

TABLE 16

Composition of the formulations prepared in order to assess the effect of polymer type on the release rate of betamethasone dipropionate from a supersaturated formulation.

| | % Excipient/Active | | | | | |
|---|---|---|---|---|---|---|
| Formulation | BMDP | PVP K90 | Co-povidone S-630 | Eudragit RSPO | Ethanol | HFA |
| Spray X | 0.050 | 2.208 | — | — | 8.00 | 89.742 |
| Spray Y | 0.050 | — | 2.304 | — | 4.000 | 93.646 |
| Spray Z | 0.050 | 1.434 | — | 1.434 | 7.500 | 89.583 |

The commercial product selected as a comparator (control) for the release studies was Diprosone® cream, (0.064% w/w, equivalent to 0.05% w/w betamethasone).

The receiver fluid was prepared by dissolving a known amount of Brij 98 into PBS followed by the addition of ethanol. The final composition of the receiver fluid was 2% Brij 98, 78% PBS and 20% ethanol. A synthetic membrane (regenerated cellulose acetate membrane with a molecular weight cut-off value of 12-14,000 Da) was mounted between the donor and receiver compartments of a Franz cell. Individually calibrated Franz cells were used where each cell has an average surface area and volume of approximately 2 $cm^2$ and 11 ml, respectively. Prior to use, the membrane was heated to 60° C. in deionised water for 1 h and rinsed with deionised water prior to mounting on to the Franz cell. The Franz cells were filled with receiver fluid and stirred continuously using PTFE-coated magnetic followers driven by a submersible magnetic stirrer plate and maintained at 32° C. The required amount of formulation (metered dose aerosol or control) was applied to the donor compartment as described. Following application of the formulations, receiver fluid (500 μL) was removed from the sampling arm at each of the sampling time points and analysed by HPLC. After each sample was removed an equal volume of pre-warmed (32° C.) receiver fluid was replaced. Time points determined were 0.25, 0.5, 0.75, 1, 1.25, 1.5, 1.75, 2, 3, 4 and 5 h. Four to five repetitions for each of the formulations were performed.

To each donor chamber of the Franz cell, a total of 50 actuations from each of the metered dose aerosol formulations was added. The weight of Diprosone® cream added was such that the amount of BMDP added was identical to the amount of BMDP from 50 actuations of the spray formulations.

Film Characterisation

The formulations were prepared by addition of the required amount of ethanol (20% w/w), active (BDP 1.76%) and antinucleating/plasticising agents (PVP K90 1.76% w/w) into a PET coated glass canister. A magnetic stirrer was inserted into the canister and the canister/valve crimped. The content of the canister was allowed to stir overnight at room temperature to ensure complete hydration of the antinucleating/plasticising agents. Following this, HFA 134a was added (76.48% w/w) into the crimped canister and the allowed to mix over 8 h.

A piece of filter paper was secured in an upright position. A ruler was placed perpendicular to the flat side of the filter paper and the filter paper thus considered 0 mm. The formulation was placed at a set distance from the filter paper with the actuator facing the paper. One hand was used to hold the formulation canister steady on the bench, while the other hand actuated the dose. After spraying a predetermined number of actuations, the filter paper was removed quickly, placed on the bench, and the wet spot of the film was outlined with an ink pen before any evaporation occurred. This was then labelled and left to dry. The image was photocopied for measurement of the diameters and the original images on filter paper were saved separately. A fresh actuator was utilised for each test and weighed before and after actuating. The discrepancy in the weights were used to account for formulation that had adhered to the actuator after being actuated form the canister.

Three indices were used to assess the shape of the film. The shortest diameter ($D_{min}$) and the longest diameter ($D_{max}$) were measured by hand in mm increments. An average of these two measurements ($D_{mean}$) was used to calculate the area assuming a perfect circle (Equation 1).

$$\text{Area} = \pi \left( \frac{D_{mean}}{2} \right)^2 \qquad \text{Equation 1}$$

Human Skin Permeation

The formulations were prepared by addition of the required amount of ethanol, active and antinucleating/plasticising agents into clear PET coated glass canisters (Table 17). A magnetic stirrer was inserted into the canister and the canister/valve crimped. The contents of the canister were allowed to stir overnight at room temperature to ensure complete hydration of the antinucleating/plasticising agents. Following this, where applicable, HFA 134a was added into the crimped canister and the contents allowed to mix over 8 h.

TABLE 17

Composition of the formulations prepared for application in the skin permeation studies

| | % Excipient/Active | | | |
| --- | --- | --- | --- | --- |
| Formulation | BMV | PVP K90 | Ethanol | HFA |
| MDA | 0.09 | 2.61 | 10.0 | 87.3 |
| Gel | 0.7 | 20.6 | 78.7 | — |

Stratum corneum was isolated from a frozen human skin sample using standard protocol. The prepared skin was mounted on a filter support and placed on the receiver section of an upright Franz cell. The donor compartment was then fixed on top of the receiver compartment and secured using Parafilm. A magnetic flea and thermostatically regulated receiver fluid (90:10 Acetate Buffer pH=4.5:EtOH) were added to each Franz cell. These cells were placed in a bath at 37° C. and allowed to equilibrate and after a few hours a blank sample was taken from each cell. The integrity of each cell was determined via inversion and an appropriate amount of formulation was applied to the donor chamber of the Franz cell. At suitable time points, a 200 µL sample was removed with a syringe (1 mL). Samples were held at room temperature until HPLC analysis. BMV was shown to be stable in the system for up to 72 h at both 4° C. and 37° C.

Example 12

Definition of a Supersaturated System

Figure 13:
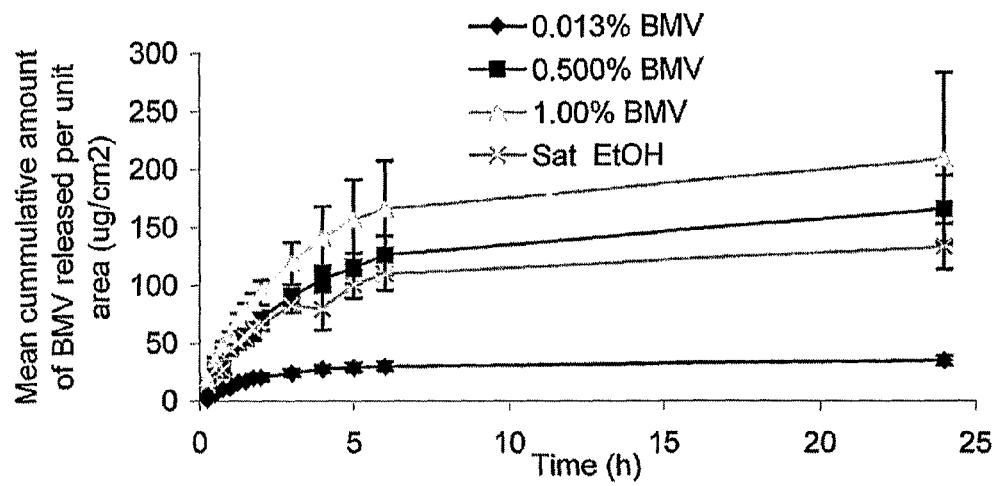

The release of BMV over a 24 h period through the porous regenerated cellulose membrane demonstrated that the concentration of drug in the formulations had a pronounced effect on both the total amount of BMV released and the rate at which it was released (FIG. 13). FIG. 13 shows the mean cumulative amount of BMV released per unit area ($\mu g/cm^2$) over t=0.25-24 h from all formulations investigated, mean±SE (n=3-5). The mean cumulative amount of BMV released after 24 h from a 0.013% BMV, 0.500% and 1.00% BMV formulation was found to be 35.11±8.94 $\mu g/cm^2$, 165.67±57.06 $\mu g/cm^2$ and 208.99±127.47 $\mu g/cm^2$, respectively. The corresponding steady state rate release was found to increase from 18.49±2.68, to 42.20±14.52, to 60.10±6.15 $\mu g\ cm^2$ for the 0.013%, 0.500% and 1.00% BMV formulations respectively (Table 18).

Figure 13A:
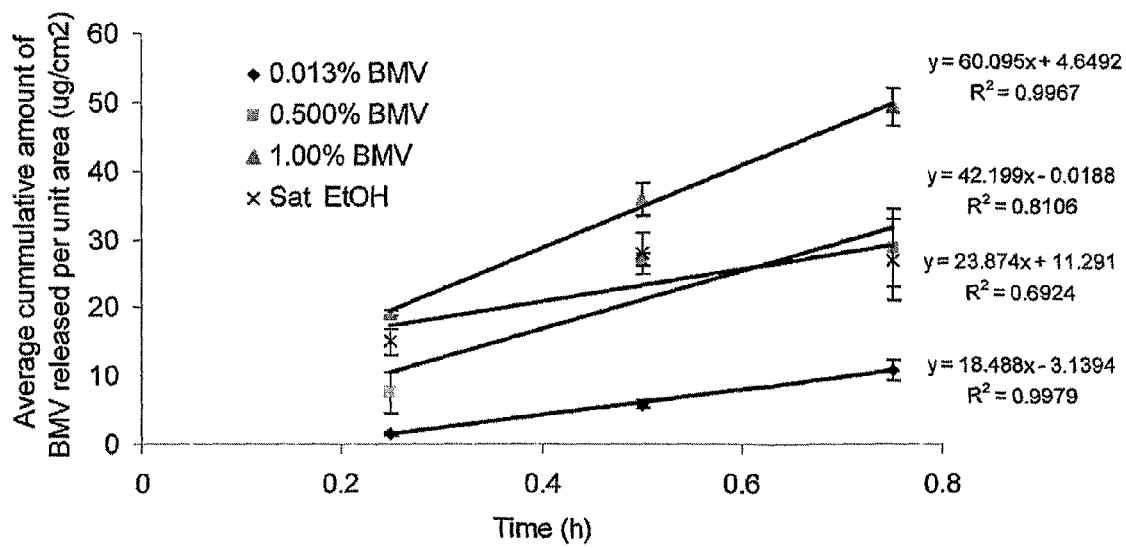

According to Fick's law of diffusion, the rate at which a compound passes from one vehicle to another through a simple membrane is not directly related to its concentration but, the thermodynamic activity of the compound in the vehicle from which it is diffusing. The thermodynamic activity of a compound within a solution is proportional to its degree of saturation. The maximum thermodynamic activity of a compound in a given solvent is 1 and this is achieved by saturating the solvent with the compound i.e., dissolving the maximum amount in the solvent. In this example the rate at which BMV diffuses through the membrane when saturated in the ethanol was 23.87±10.81 $\mu g\ cm^2$ and this represents the diffusion rate of BMV when saturated i.e. at a thermodynamic activity of 1. Surprisingly when the BMV was applied to the membrane using the novel spray formulation at a saturated concentration (1.00% BMV) the release rate (the initial gradients shown in FIG. 13a) was 2.5-fold greater than the saturated ethanol solution. When applied using 0.500% BMV and 0.013% BMV the initial release rate was not significantly different (p<0.05, ANOVA) compared to the ethanol system. These results illustrate that the BMV is present as a 2.5× supersaturated system on the membrane after application from an initially saturated formulation. When the BMV was formulated at 10-50% of its totally saturated concentration it generated a saturated solution when upon application to the membrane released the drug at a rate equivalent to the saturated ethanol solution.

The dramatic increase in flux from the novel formulations appears to be as a result of the interaction between the instantly evaporating HFA solvent and the co-solvent that generates a highly supersaturated formulation on the surface of the membrane. This effect occurs when the drug is included at >50% of its total saturated concentration in the HFA/ethanol mix. The ability of this novel formulation approach to be stored as saturated systems prior to application and generate a highly saturated state upon application is highly advantageous for topical drug delivery.

TABLE 18

Summary of steady state flux of formulations containing equivalent concentrations of ethanol and co-povidone, but varying HFA concentrations and 0.013%, 0.500%, 1.00% BMV. The control was a BMV saturated in ethanol solution.

| Formulation | Steady state flux, mean ± SE (n = 3-5) t = 0 to 0.75 h |
| --- | --- |
| 0.013% BMV (n = 5) | 18.49 ± 2.68 |
| 0.500% BMV (n = 4) | 42.20 ± 14.52 |
| 1.00% BMV (n = 3) | 60.10 ± 6.15 |
| BMV in saturated Ethanol (n = 4) | 23.87 ± 10.81 |

Example 13

Drug Stability in a Supersaturated Metered Dose Aerosol

Upon storage in an ethanol/HFA mixture for four weeks a significant proportion of the originally included BMV appeared to be lost, presumably due to chemical degradation (Table 19). However, when acidified ethanol was used as the co-solvent in the formulation there was no significant ($p<0.05$, ANOVA) difference in the BMV recovered from the formulations after 4 weeks compared to that at the initiation of the study. The inclusion of the drug in a HFA/isopropyl alcohol mixture led to a small, but significant ($p>0.05$, ANOVA) reduction in the relative concentration of BMV.

TABLE 19

Summary of the relative BMV concentrations in the novel spray formulation after 4 weeks storage at room temperature using ethanol (BMV Cont), isopropyl alcohol (BMVIPA) and acidified ethanol (BMVeth3.5) n = 3 mean ± SD.

| Formulation | Relative drug concentration 0 weeks (%) | Relative drug concentration 4 weeks (%) |
| --- | --- | --- |
| BMV Cont | 77.66 ± 3.62 | 63.39 ± 6.09 |
| BMVIPA | 95.59 ± 1.41 | 92.57 ± 1.14 |
| BMVeth3.5 | 98.45 ± 1.67 | 93.64 ± 5.54 |

Example 14

The Production of a Saturated Salicylic Acid Metered Dose Aerosol

Figure 14:
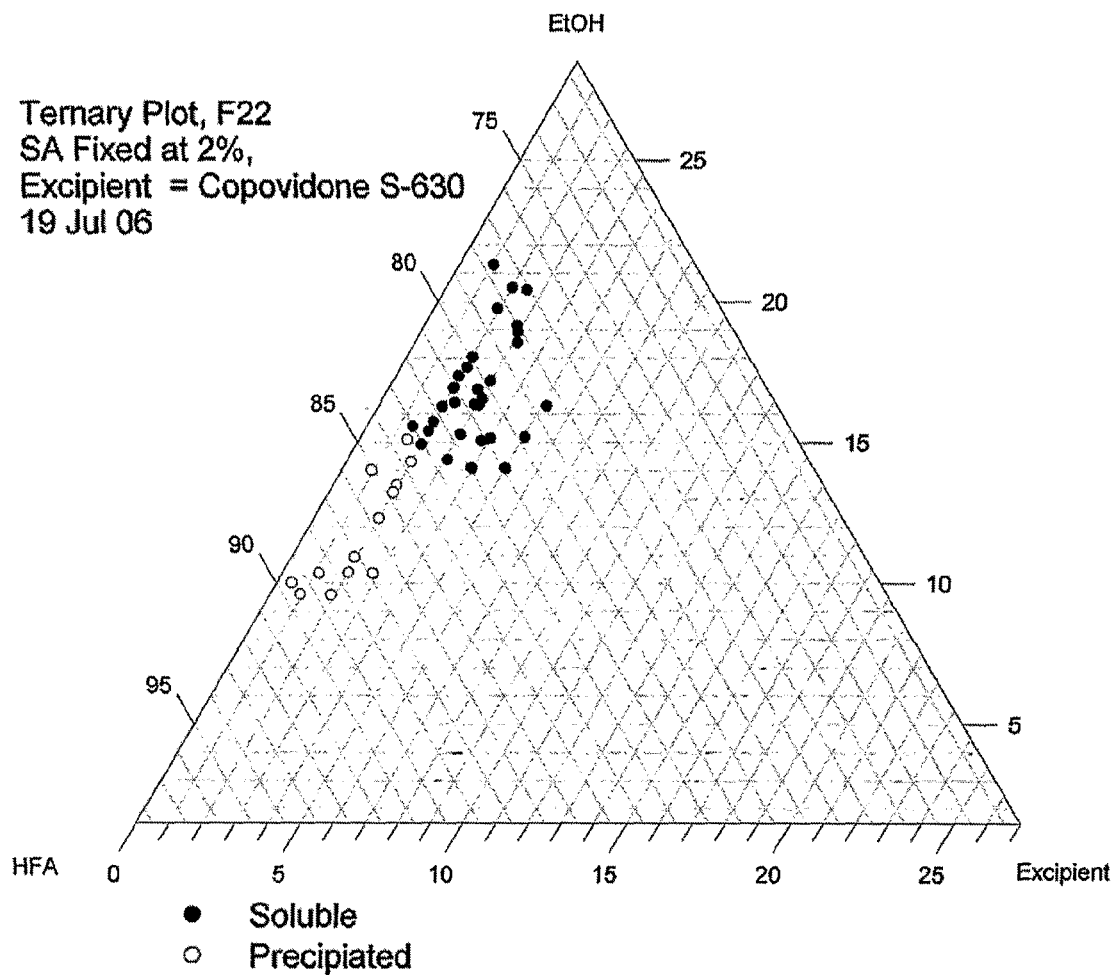

FIG. 14 is a ternary phase plot of 2% salicylic acid at various excipient compositions. Salicylic acid was solubilised within an ethanol, hydrofluoroalkane mixture with co-povidone S-630. The ternary plot indicates that a saturated system was able to be formed with 2% salicylic acid and 83% HFA by simply varying the level of ethanol in the formulation (FIG. 14).

Example 15

The Effect of Polymer on the Release Rate of Beclomethasone Dipropionate

Figure 15:
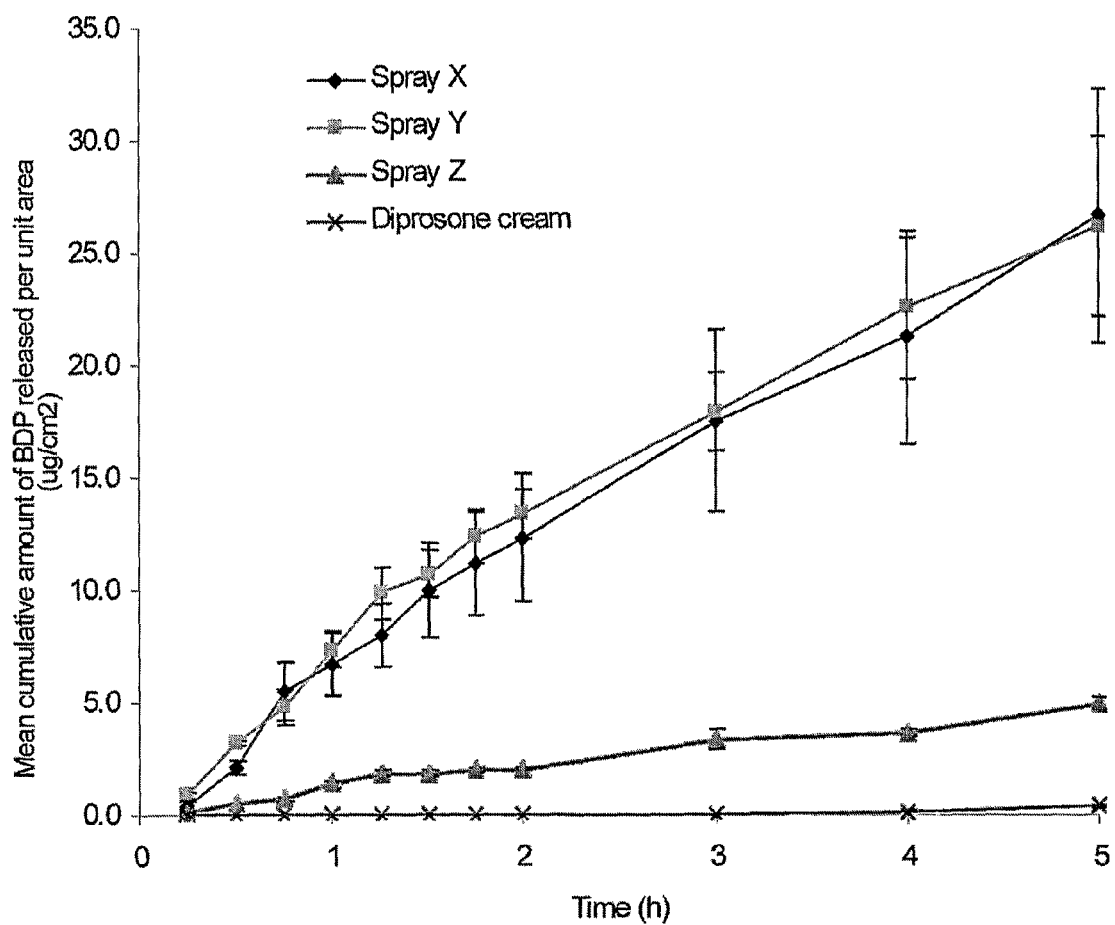

FIG. 15 shows mean cumulative amount of BMDP released per unit area (µg/cm$^2$) over t=0.25-5 h from three novel spray formulations containing polyvinyl pyrrolidone (Spray X, PVP K90), co-povidone (Spray Y) and of Eudragit and PVP (Spray Z) compared to a commercial comparator diprosone, mean±SE (n=3-5). Regardless whether polyvinyl pyrrolidone (Spray X, PVP K90) or co-povidone (Spray Y) was used in the saturated spray formulations they generated a very similar release rate of BMDP over the 5 h period (FIG. 15). However, the cumulative amount of BMDP released after 5 h for Spray Z (Eudragit and PVP) was significantly lower ($p<0.05$, ANOVA) at 0.949±0.176 µg/cm$^2$.

All of the novel spray formulations tested displayed a significantly ($p<0.05$, ANOVA) higher release of the BDP compared to the commercial cream (Diprosone) where the cumulative amount of BDP released after 5 h was found to be 0.062±0.011 µg/cm$^2$.

Example 16

The Production of a Saturated Benzoyl Peroxide Metered Dose Aerosol

Figure 16:
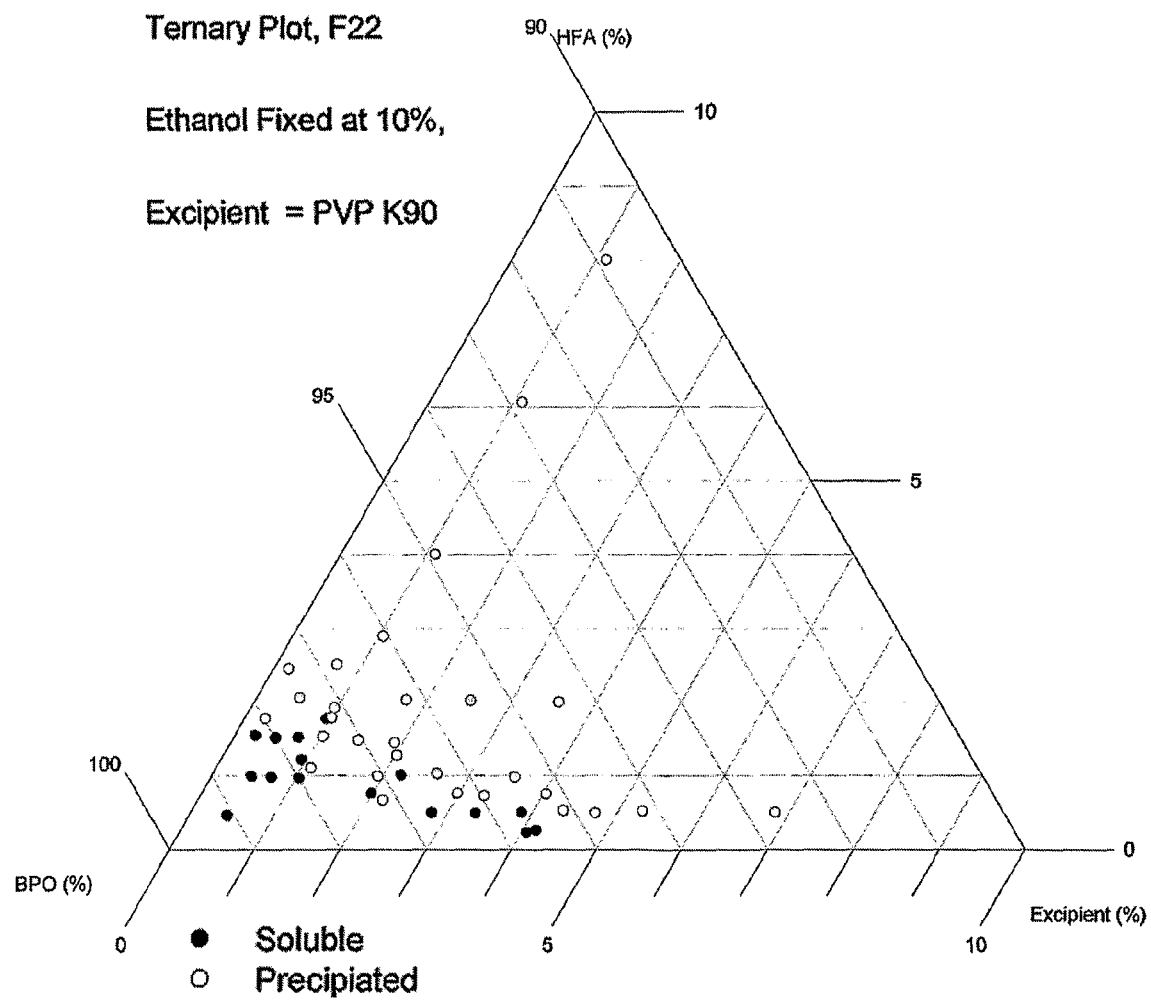

FIG. 16 is a ternary phase plot of benzoyl peroxide at various excipient compositions. Benzoyl peroxide (BPO) was solubilised within an ethanol, hydrofluoroalkane mixture with PVP K90. The ternary plot indicates that a saturated system could be formed with 1% BPO and 98% HFA using 10% ethanol in the formulation (FIG. 16).

Example 17

Effect of Spray Distance Upon Film Formation

Figure 17:
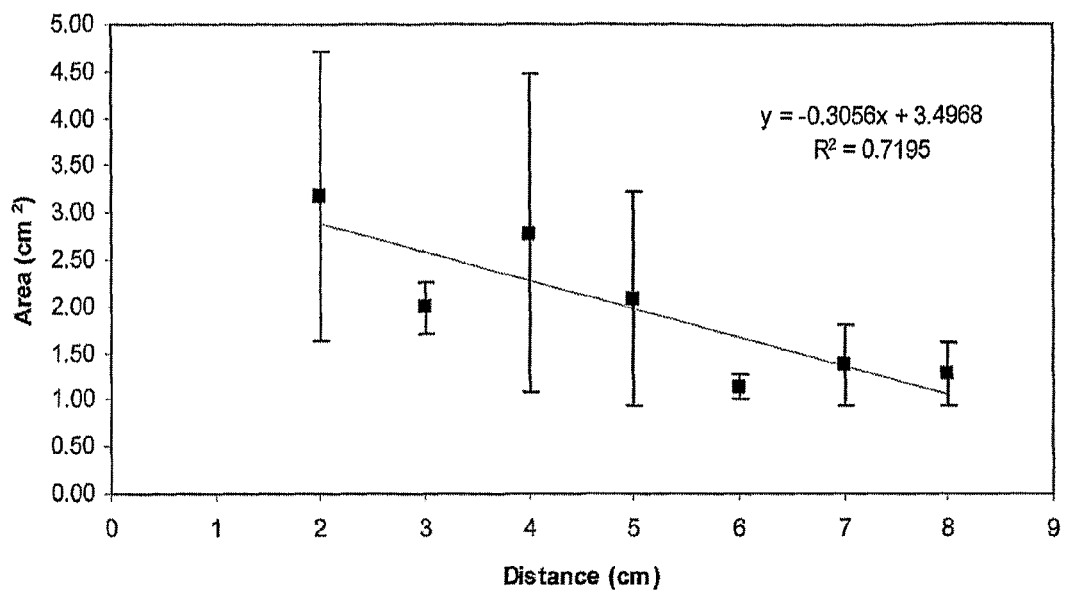

In order to evaluate what effect the distance between the formulation and the intended deposition site of the film had on its characteristics, a single shot of the Spray formulation was actuated at different set distances from its target surface (FIG. 17).

FIG. 17 shows the effect on the area of the film by varying distance of the formulation from the filter paper. Data derived from a single actuation of the 20% EtOH 1:1 PVP K90: BDP formulation, mean±sd (n=4)

A general decrease in film area as the distance between the formulation and the filter paper increased was observed. The reduction in variability of the film as the spray distance increase suggested that the optimal distance was approx >6 cm.

Example 18

Effect of Spray Number Upon Film Formation

Figure 18:
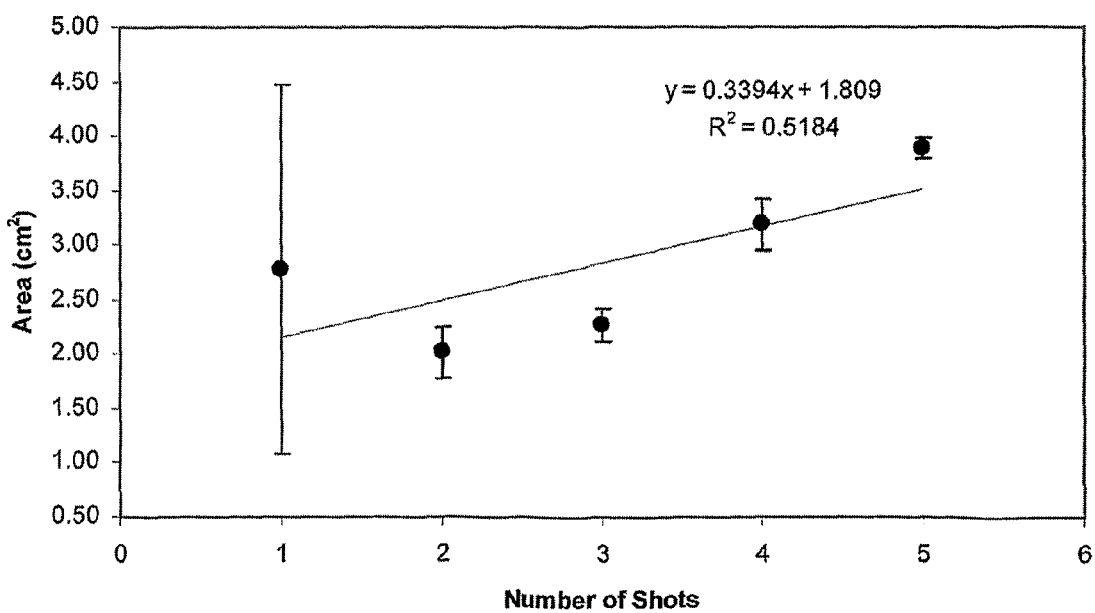

The area of the film generated by the novel Spray formulation increased as the number of actuations was increased (FIG. 18). The variability of the dosing also decreased as the number of actuations was increased.

FIG. 18 shows the effect on the area of the film with increase in the number of actuations of formulation. The distance of the formulation from the filter paper was kept constant at 4 cm and the 20% EtOH 1:1 PVP K90: BDP formulation was used, mean±SD (n=4)

The reduction in variability of the film as the number of actuation was increased suggested that the optimal number of actuations was 2 or greater.

Example 19

Drug Permeation Through Human Skin

The amount of BDP that permeated across the human Stratum corneum was significantly greater (p<0.05, ANOVA) using the novel Spray formulation after 5 h compared to the gel (FIG. 19). Although the gel formulation continued to release after 5 h the novel formulation did not and the drug concentration in the receiver fluid remained constant.

FIG. 19 shows the mean cumulative amount of BMV permeating across the Stratum corneum per unit area ($\mu g/cm^2$) during t=0.25-7 h from a novel spray formulation (MDA) compared to a gel (BMV gel) comprising similar excipients except for the inclusion of hydrofluoroalkane propellant, mean±SE (n=6-8).

The difference between the diffusion of BMV from the gel and the Spray formulations illustrated that the inclusion of the HFA in the novel spray formulation is fundamental to allow enhanced permeation of the active agent into the skin.

Example 20

Exemplary Formulations

TABLE 20

Placebo formulations

Composition (Theoretical) %

| Formulation | PVP K90 | PVA 40% hydrolysed | Eudragit RSPO | Copovidone S-630 | Poloxamer 407 | H2O | Ethanol | HFA |
|---|---|---|---|---|---|---|---|---|
| 7 | 1.000% | — | — | — | — | — | 10.000% | 89.000% |
| 18 | 2.610% | — | — | — | — | — | 20.000% | 77.390% |
| 20 | 0.468% | — | — | 0.467 | — | — | 15.000% | 84.065% |
| 22 | — | — | — | 2.000 | — | — | 10.000% | 88.000% |
| 27 | 0.468% | 0.467 | — | — | — | 0.50% | 15.000% | 83.865% |
| 29 | 0.468% | 0.467 | — | — | — | 1.00% | 15.000% | 83.065% |
| 36 | 0.500% | — | 0.500% | — | — | — | 10.000% | 89.000% |
| 39 | 0.500% | — | — | — | 0.500% | — | 10.000% | 89.000% |

TABLE 21

Composition of BMV MedSpray formulations proposed for Stability Studies

Composition (Theoretical) %

| Formulation | BMV | Copovidone-S630 | PVP K90 | Eudragit RSPO | Ethanol | IPA | HFA |
|---|---|---|---|---|---|---|---|
| F7 v26 | 0.0294 | — | 1.7995 | — | 8.7974 | — | 89.3737 |
| F22 v41 | 0.0294 | 1.1247 | — | — | 4.9485 | — | 93.8974 |
| F36 v26 | 0.0294 | — | 1.5183 | 1.5183 | 8.7974 | — | 88.1366 |
| F22 IPA v34 | 0.0294 | 1.3496 | — | — | — | 6.5981 | 92.0229 |

TABLE 22

Composition of Spray formulations for Stability Studies

Composition (Theoretical) %

| Formulation | SA | PVP K25 | Endragit RSPO | Copovidone-S-630 | Ethanol | HFA |
|---|---|---|---|---|---|---|
| F14 ai | 2.000 | — | 1.764 | — | 9.702 | 86.534 |
| F22 at | 2.000 | — | — | 2.558 | 15.631 | 79.811 |
| F57 ab | 2.000 | 1.985 | — | — | 19.404 | 76.612 |
| F58 ad | 2.000 | 1.294 | 1.294 | — | 19.404 | 76.009 |

TABLE 23

BDP Spray formulations for release studies

Composition (Theoretical)%

| Formulation | BDP | PVP K90 | Copovidone S-630 | Eudragit RSPO | Ethanol | HFA |
|---|---|---|---|---|---|---|
| F7 BDP | 0.050 | 2.208 | — | — | 8.500 | 89.242 |
| F22 BDP | 0.050 | — | 1.920 | — | 4.00 | 94.03 |
| F36 BDP | 0.050 | 1.340 | — | 1.340 | 8.000 | 89.270 |

REFERENCES

Hadgraft, J., 2004. Skin deep. European Journal of Pharmaceutics and Biopharmaceutics, 58, 291-299.

Moser, K., Kriwet, K., Froehlich, C., Kalia, Y. N., Guy, R. H., 2001a. Supersaturation: Enhancement of skin penetration and permeation of a lipophilic drug. Pharm. Res., 18, 1006-1011.

Moser, K., Kriwet, K., Froehlich, C., Naik, A., Kalia, Y. N., Guy, R. H., 2001b. Permeation enhancement of a highly lipophilic drug using supersaturated systems. J. Pharm. Sci., 90, 607-616.

Moser, K., Kriwet, K., Kalia, Y. N., Guy, R. H., 2001c. Stabilization of supersaturated solutions of a lipophilic drug for dermal delivery. Int. J. Pharm., 224, 169-176.

Ranade, V. V., 1995. Drug Delivery Systems. CRC Press, New York, pp. 177-208.

Thomas, B. J., Finnin, B. C., 2004. The transdermal revolution. Drug Discovery Today, 9, 697-703.

Ting, W. W., Vest, C. D., Sontheimer, R. D., 2004. Review of traditional and novel modalities that enhance the permeability of local therapeutics across the Stratum corneum. Int. J. Dermatol., 43, 538-547.

Vervaet, C., Byron, P. R., 1999. Drug-surfactant-propellant interactions in HFA-formulations. Int. J. Pharm., 186, 13-30.

Yong-Hong Liao. Studies on the Stabilisation and Formulation of Proteins for Airway Delivery. 2002.

The invention claimed is:

1. A pharmaceutical formulation capable of forming a film on topical administration, said formulation comprising a preparation of a pharmaceutical, a solvent therefor, a film-forming agent, and a propellant, wherein the formulation is a monophasic solution and the pharmaceutical is present at at least 80% saturation under conditions of use, and wherein there is no undissolved pharmaceutical in the formulation.

2. The formulation of claim 1, wherein the pharmaceutical is present at at least 90% saturation.

3. The formulation of claim 1, wherein the pharmaceutical is present at at least 95% saturation.

4. The formulation of claim 1, wherein the pharmaceutical is present at, or close to, 100% saturation.

5. The formulation of claim 1, comprising an antinucleating agent.

6. The formulation of claim 5, wherein said antinucleating agent is selected from the group consisting of: poly(vinyl alcohol)(PVA), methyl cellulose, ethyl cellulose, hydroxypropylmethylcellulose, hydroxypropylcellulose, glycol esters, polyacrylic acid, and derivatives thereof.

7. The formulation of claim 1, wherein said pharmaceutical is selected from the group consisting of: local antipruritics; local anaesthetics; antihistamines; corticosteroids; topical preparations for psoriasis; topical preparations for acne; topical antibacterials for acne; dermatological drugs; topical retinoids and related preparations for acne; other topical preparations for acne; topical antibacterials; topical antifungals; antiviral preparations; preparations for minor cuts and abrasions; topical circulatory preparations; heparinoid antiperspirants; non-steroidal anti-inflammatories; actinic keratosis treatments; capsaicin; and combinations thereof.

8. The formulation of claim 1, for application to a body surface selected from: skin, nail, wounds, oral mucosa, vagina, rectum, anus, nose, and teeth.

9. The formulation of claim 1, wherein said film-forming agent is selected from the group consisting of polyvinyl pyrrolidone, polyvinyl alcohol, acrylic polymers, acrylic copolymers, methacrylate polymers, methacrylate copolymers, poly (vinyl acetate), cellulose based polymers and cellulose based co-polymers.

10. The formulation of claim 9, wherein said film-forming component is PVP.

11. The formulation of claim 9, wherein said film-forming component is PVA.

12. The formulation of claim 1, wherein said film-forming agent is such that the formulation is capable of forming a hydrogel on skin.

13. The formulation of claim 1, wherein said film-forming agent is present in an amount of between 0.1 and 40% w/w inclusive.

14. The formulation of claim 13, wherein said film-forming agent is present in an amount of between 0.1 and 10% w/w inclusive.

15. The formulation of claim 13, wherein said film-forming agent is present in an amount of between 0.1 and 4% w/w inclusive.

16. The formulation of claim 1, comprising a plasticiser.

17. The formulation of claim 16, wherein said plasticiser is selected from the group consisting of: water, glycerol, polyethylene glycol, oleic acid, citric acid, phosphate esters, fatty acid esters, glycol derivatives, hydrocarbons and hydrocarbon derivatives, adipic acid/butanediol polyesters, epoxidised soya oils, diethyl phthalate, dibutyl phthalate, citric acid esters, castor oil, triacetin, chlorinated paraffins, and mixtures thereof.

18. The formulation of claim 16, wherein said plasticiser is present in an amount of between 0.1 and 40% w/w inclusive.

19. The formulation of claim 16, wherein said plasticiser is present in an amount of between 0.1 and 10% w/w inclusive.

20. The formulation of claim 16, wherein said plasticiser is present in an amount of between 0.1 and 4% w/w inclusive.

21. The formulation of claim 1, wherein said propellant is one or more hydrofluoroalkanes.

22. The formulation of claim 1, wherein said solvent is selected from the group consisting of: water, cyclomethicone, benzyl alcohol, propylene glycol, polyethylene glycol, propylene carbonate, ethanol, dimethyl sulphoxide, glycerin, isopropyl alcohol, isopropyl myristate, oleic acid, and mixtures thereof.

23. The formulation of claim 22, wherein said solvent comprises benzyl alcohol in an amount of up to 2.5% w/w.

24. The formulation of claim 1, wherein said solvent is present in an amount of up to 40%.

25. The formulation of claim 1, wherein said solvent is selected from the group consisting of: ethanol and isopropyl alcohol.

26. The formulation of claim 25, wherein said solvent is ethanol in an amount of no more than 15% w/w.

27. The formulation of claim 25, wherein said solvent is ethanol and the amount of said ethanol is no more than 10% w/w.

28. The formulation of claim 1, having a pH adjusted to enhance stability of the pharmaceutical.

29. The formulation of claim 1, comprising a plasticiser selected from the group consisting of: polyethylene glycol, poly(meth)acrylate, polyvinyl pyrrolidone, and combinations thereof.

30. The formulation of claim 29, comprising between 1 and 5% w/w, inclusive, polyethylene glycol.

31. The formulation of claim 1, wherein the nature and concentration of the film-forming component are selected such that a film is formed after the evaporation of a portion of the solvent, wherein the film-forming component is selected from the group consisting of polyvinyl pyrrolidone, polyvinyl alcohol, acrylic polymers, acrylic copolymers, methacrylate polymers, methacrylate copolymers, poly (vinyl acetate), cellulose based polymers and cellulose based co-polymers.

32. An aerosol dispenser comprising a reservoir of the formulation of claim 1.

33. A method for the treatment of a condition with a drug suitable for the treatment of said condition, comprising applying an effective amount of said drug to a patient in need thereof by administering the formulation of claim 1 to a topical surface of said patient.

* * * * *